US011564594B2

(12) United States Patent
Merrell et al.

(10) Patent No.: US 11,564,594 B2
(45) Date of Patent: *Jan. 31, 2023

(54) SHOE-BASED ANALYSIS SYSTEM

(71) Applicant: Nano Composite Products, Inc., Orem, UT (US)

(72) Inventors: Aaron Jake Merrell, Orem, UT (US); Anton E. Bowden, Lindon, UT (US); David T. Fullwood, Lindon, UT (US); Matthew Kirk Seeley, Spanish Fork, UT (US); Gavin Quinn Collins, Provo, UT (US); Parker Gary Rosquist, Bluffdale, UT (US); William Fredrick Christensen, Provo, UT (US)

(73) Assignee: Nano Composite Products, Inc., Orem, UT (US)

(*) Notice: Subject to any disclaimer, the term of this patent is extended or adjusted under 35 U.S.C. 154(b) by 621 days.

This patent is subject to a terminal disclaimer.

(21) Appl. No.: 16/562,808

(22) Filed: Sep. 6, 2019

(65) Prior Publication Data

US 2020/0069220 A1 Mar. 5, 2020

Related U.S. Application Data

(63) Continuation of application No. 14/990,763, filed on Jan. 7, 2016, now Pat. No. 10,405,779.

(Continued)

(51) Int. Cl.
*A61B 5/00* (2006.01)
*A61B 5/103* (2006.01)
(Continued)

(52) U.S. Cl.
CPC ............. *A61B 5/1038* (2013.01); *A43B 3/34* (2022.01); *A43B 7/24* (2013.01); *A61B 5/112* (2013.01);
(Continued)

(58) Field of Classification Search
CPC ....... A61B 5/1038; A61B 5/112; A61B 5/486; A61B 5/6807; A61B 5/7405; A61B 5/742; A61B 2562/0261; A43B 3/34; A43B 7/24
See application file for complete search history.

(56) References Cited

U.S. PATENT DOCUMENTS 3,321,592 A 5/1967 Miller
3,748,373 A 7/1973 Remy
(Continued)

FOREIGN PATENT DOCUMENTS

CN 200994779 Y 12/2007
CN 101219050 A 7/2008
(Continued)

OTHER PUBLICATIONS

Sun et al., "Energy Absorption Capability of Nanocomposites: A review", Composites Science and Technology, vol. 69, No. 14, 2009, pp. 2392-2409.
(Continued)

*Primary Examiner* — May A Abouelela
(74) *Attorney, Agent, or Firm* — Brake Hughes Bellermann LLP

(57) ABSTRACT

In one example, an apparatus. includes a shoe having a sole with at least a portion of foam replaced with a composite polymeric foam, at least one probe disposed in the composite polymeric foam, a voltage detector coupled to the probe that detects voltage data generated by the composite polymeric foam, and a transformation module that converts voltage data generated by the composite polymeric foam in response to deformation events into GRF, acceleration, or pressure data. In another example, a method includes receiving voltage data produced by composite polymeric foam, the composite polymeric foam providing support and padding in the sole of a shoe, converting the voltage data to force data,
(Continued)

comparing the force data to a profile, and transmitting, when the force data fails to fall within a threshold of the profile, a feedback signal to a physical feedback device, the feedback signal indicating a difference with the profile.

20 Claims, 14 Drawing Sheets

Related U.S. Application Data

(60) Provisional application No. 62/100,851, filed on Jan. 7, 2015.

(51) Int. Cl.
*A61B 5/11* (2006.01)
*A43B 7/24* (2006.01)
*A43B 3/34* (2022.01)

(52) U.S. Cl.
CPC ............ *A61B 5/486* (2013.01); *A61B 5/6807* (2013.01); *A61B 5/742* (2013.01); *A61B 5/7405* (2013.01); *A61B 2562/0261* (2013.01)

(56) References Cited

U.S. PATENT DOCUMENTS

| | | | |
|---|---|---|---|
| 3,794,790 A | | 2/1974 | Leyland |
| 4,060,705 A | | 11/1977 | Peachey |
| 4,144,877 A | | 3/1979 | Frei et al. |
| 4,172,216 A | | 10/1979 | O'shea |
| 4,258,100 A | | 3/1981 | Fujitani et al. |
| 4,624,796 A | | 11/1986 | Giniewicz et al. |
| 4,664,971 A | | 5/1987 | Soens |
| 4,762,970 A | | 8/1988 | Brinsley |
| 4,771,394 A | | 9/1988 | Cavanagh |
| 4,777,346 A | | 10/1988 | Swanton, Jr. |
| 4,808,336 A | | 2/1989 | Rubner et al. |
| 4,951,985 A | | 8/1990 | Pong et al. |
| 5,060,527 A | | 10/1991 | Burgess |
| 5,132,583 A | | 7/1992 | Chang |
| 5,323,650 A | | 6/1994 | Fullen et al. |
| 5,373,651 A | | 12/1994 | Wood |
| 5,441,301 A | | 8/1995 | Breed et al. |
| 5,449,002 A * | | 9/1995 | Goldman .............. A43B 17/00 600/595 |
| 5,510,812 A | | 4/1996 | O'mara et al. |
| 5,540,996 A | | 7/1996 | Tanzilli et al. |
| 5,568,659 A | | 10/1996 | Fogel |
| 5,592,759 A | | 1/1997 | Cox |
| 5,637,389 A | | 6/1997 | Colvin et al. |
| 5,695,859 A | | 12/1997 | Burgess |
| 5,702,629 A | | 12/1997 | Cui et al. |
| 5,775,715 A | | 7/1998 | Vandergrift |
| 5,855,818 A | | 1/1999 | Gan et al. |
| 5,856,644 A | | 1/1999 | Burgess |
| 5,951,908 A | | 9/1999 | Cui et al. |
| 6,033,370 A * | | 3/2000 | Reinbold ............. A61B 5/6805 600/595 |
| 6,121,869 A | | 9/2000 | Burgess |
| 6,126,874 A | | 10/2000 | Dillon et al. |
| 6,265,466 B1 | | 7/2001 | Glatkowski et al. |
| 6,360,597 B1 | | 3/2002 | Hubbard, Jr. |
| 6,430,843 B1 | | 8/2002 | Potter et al. |
| 6,485,432 B1 | | 11/2002 | Stasz et al. |
| 6,506,153 B1 | | 1/2003 | Littek et al. |
| 6,529,122 B1 | | 3/2003 | Magnussen et al. |
| 6,534,430 B2 | | 3/2003 | Makino et al. |
| 6,555,767 B1 | | 4/2003 | Lockery et al. |
| 6,724,195 B2 | | 4/2004 | Lurtz |
| 6,780,505 B1 | | 8/2004 | Klett et al. |
| 6,925,851 B2 | | 8/2005 | Reinbold et al. |
| 6,978,684 B2 | | 12/2005 | Nurse |
| 7,059,028 B2 | | 6/2006 | Lammer |
| 7,059,197 B2 | | 6/2006 | Son et al. |
| 7,147,214 B2 | | 12/2006 | Klett et al. |
| 7,225,565 B2 | | 6/2007 | Dibenedetto et al. |
| 7,426,873 B1 | | 9/2008 | Kholwadwala et al. |
| 7,443,082 B2 | | 10/2008 | Grumm |
| 7,479,878 B2 | | 1/2009 | Maki et al. |
| 7,506,460 B2 | | 3/2009 | Dibenedetto et al. |
| 7,509,835 B2 | | 3/2009 | Beck |
| 7,587,937 B2 | | 9/2009 | Haselhurst et al. |
| 7,695,647 B2 | | 4/2010 | Smela et al. |
| 7,854,173 B2 | | 12/2010 | Cheng et al. |
| 7,935,415 B1 | | 5/2011 | Hansen et al. |
| 7,947,773 B2 | | 5/2011 | Hansen et al. |
| 7,997,125 B2 | | 8/2011 | Kaya et al. |
| 8,210,994 B2 | | 7/2012 | Chang et al. |
| 8,305,358 B2 | | 11/2012 | Klinghult et al. |
| 8,361,608 B1 | | 1/2013 | Hansen et al. |
| 8,371,174 B2 | | 2/2013 | Chen et al. |
| 8,544,337 B2 | | 10/2013 | Kuczynski et al. |
| 8,628,485 B2 | | 1/2014 | Wilson et al. |
| 8,631,703 B2 | | 1/2014 | Nagai et al. |
| 8,669,755 B2 | | 3/2014 | Kato et al. |
| 8,758,892 B2 | | 6/2014 | Bergin et al. |
| 8,850,897 B2 | | 10/2014 | Eichhorn et al. |
| 8,904,877 B2 | | 12/2014 | Burke et al. |
| 8,984,954 B2 | | 3/2015 | Merrell et al. |
| 9,044,593 B2 | | 6/2015 | Li et al. |
| 9,099,224 B2 | | 8/2015 | Choi et al. |
| 9,192,816 B2 * | | 11/2015 | Molyneux .............. A43B 7/145 |
| 9,279,734 B2 * | | 3/2016 | Walker ...................... G01L 1/18 |
| 10,070,680 B2 * | | 9/2018 | Molyneux ................ A43B 3/34 |
| 10,658,567 B2 | | 5/2020 | Merrell et al. |
| 11,329,212 B2 | | 5/2022 | Merrell et al. |
| 2002/0198069 A1 | | 12/2002 | Snyder et al. |
| 2003/0009985 A1 | | 1/2003 | Kirtley |
| 2003/0194544 A1 | | 10/2003 | Tobita et al. |
| 2003/0213939 A1* | | 11/2003 | Narayan ................ B82Y 10/00 252/500 |
| 2005/0044751 A1 | | 3/2005 | Alaimo et al. |
| 2005/0101719 A1 | | 5/2005 | Ishihara |
| 2005/0124864 A1 | | 6/2005 | Mack et al. |
| 2005/0174243 A1 | | 8/2005 | Musil |
| 2005/0258717 A1 | | 11/2005 | Mullen |
| 2006/0260058 A1 | | 11/2006 | Schmidt |
| 2006/0272429 A1 | | 12/2006 | Ganapathi et al. |
| 2007/0056081 A1 | | 3/2007 | Aspray |
| 2007/0068244 A1 | | 3/2007 | Billing et al. |
| 2007/0084293 A1 | | 4/2007 | Kaiserman et al. |
| 2007/0135878 A1 | | 6/2007 | Lachenbruch et al. |
| 2007/0157488 A1 | | 7/2007 | Guzman |
| 2008/0066564 A1 | | 3/2008 | Hayakawa et al. |
| 2008/0067618 A1 | | 3/2008 | Wang et al. |
| 2008/0067619 A1 | | 3/2008 | Farahani et al. |
| 2008/0195187 A1 | | 8/2008 | Li et al. |
| 2008/0277631 A1 | | 11/2008 | Smela et al. |
| 2009/0165569 A1 | | 7/2009 | Taya et al. |
| 2009/0226696 A1 | | 9/2009 | Simpson |
| 2009/0240171 A1 | | 9/2009 | Morris Bamberg et al. |
| 2009/0288259 A1 | | 11/2009 | Lean et al. |
| 2009/0302714 A1 | | 12/2009 | Kim |
| 2010/0014556 A1 | | 1/2010 | Huynh |
| 2010/0063779 A1 | | 3/2010 | Schrock et al. |
| 2010/0126273 A1 | | 5/2010 | Lim et al. |
| 2010/0271174 A1 | | 10/2010 | Kaminska et al. |
| 2010/0305478 A1* | | 12/2010 | Ordway ............... A61B 5/1038 600/587 |
| 2010/0324698 A1 | | 12/2010 | Sverrisson et al. |
| 2011/0054358 A1 | | 3/2011 | Kim et al. |
| 2011/0054359 A1 | | 3/2011 | Sazonov et al. |
| 2011/0192049 A1 | | 8/2011 | Auger et al. |
| 2011/0192564 A1 | | 8/2011 | Mommer et al. |
| 2011/0214501 A1 | | 9/2011 | Ross et al. |
| 2011/0226066 A1 | | 9/2011 | Anand et al. |
| 2011/0265973 A1 | | 11/2011 | Scalia, Jr. |
| 2012/0024061 A1 | | 2/2012 | Chiang |
| 2012/0036939 A1 | | 2/2012 | Jarjour et al. |
| 2012/0048528 A1 | | 3/2012 | Bergin et al. |
| 2012/0055257 A1 | | 3/2012 | Shaw-klein |
| 2012/0082950 A1 | | 4/2012 | Li et al. |
| 2012/0166091 A1 | | 6/2012 | Kim et al. |

(56) References Cited

U.S. PATENT DOCUMENTS

| | | | |
|---|---|---|---|
| 2012/0193572 A1 | 8/2012 | Mackay | |
| 2012/0234111 A1* | 9/2012 | Molyneux | G06F 3/0334 361/679.01 |
| 2012/0289866 A1 | 11/2012 | Irby et al. | |
| 2012/0291564 A1* | 11/2012 | Amos | A43B 13/141 73/862.041 |
| 2013/0026411 A1 | 1/2013 | Jenninger et al. | |
| 2013/0074248 A1 | 3/2013 | Evans et al. | |
| 2013/0079693 A1 | 3/2013 | Ranky et al. | |
| 2013/0123665 A1 | 5/2013 | Mariani et al. | |
| 2013/0130843 A1 | 5/2013 | Burroughs et al. | |
| 2013/0224458 A1 | 8/2013 | Bolliou | |
| 2014/0013862 A1 | 1/2014 | Lind | |
| 2014/0039082 A1 | 2/2014 | Peterson et al. | |
| 2014/0182063 A1 | 7/2014 | Crawford et al. | |
| 2014/0183403 A1 | 7/2014 | Peterson et al. | |
| 2014/0230563 A1* | 8/2014 | Huang | A61B 5/7225 73/841 |
| 2014/0260653 A1 | 9/2014 | Merrell et al. | |
| 2014/0260677 A1* | 9/2014 | Dojan | A43B 13/14 73/862.045 |
| 2014/0338458 A1 | 11/2014 | Wang et al. | |
| 2014/0350435 A1 | 11/2014 | Lam | |
| 2015/0101417 A1 | 4/2015 | Carroll et al. | |
| 2015/0177079 A1 | 6/2015 | Eichhorn et al. | |
| 2015/0182844 A1 | 7/2015 | Jang | |
| 2015/0283353 A1 | 10/2015 | Kohn et al. | |
| 2015/0289594 A1* | 10/2015 | Rushbrook | A43B 3/34 12/142 T |
| 2016/0011091 A1* | 1/2016 | Huang | A61B 5/1038 73/841 |
| 2016/0021972 A1* | 1/2016 | Grelle | A43B 7/24 36/140 |
| 2016/0076954 A1 | 3/2016 | Bowden et al. | |
| 2016/0163959 A1* | 6/2016 | Merrell | G01L 1/20 73/768 |
| 2016/0166178 A1 | 6/2016 | Fuss et al. | |
| 2016/0181506 A1 | 6/2016 | Sirbuly et al. | |
| 2016/0341610 A1* | 11/2016 | Merrell | G01L 1/16 |
| 2017/0077838 A1 | 3/2017 | Wang et al. | |
| 2017/0303637 A1* | 10/2017 | Grand | A43B 7/145 |
| 2020/0388749 A1 | 12/2020 | Merrell et al. | |

FOREIGN PATENT DOCUMENTS

| | | |
|---|---|---|
| CN | 101669683 A | 3/2010 |
| CN | 201846875 U | 6/2011 |
| CN | 102144056 A | 8/2011 |
| CN | 102175356 A | 9/2011 |
| CN | 202396563 U | 8/2012 |
| CN | 202635729 U | 1/2013 |
| CN | 103110235 A | 5/2013 |
| CN | 103142236 | 6/2013 |
| CN | 103900741 A | 7/2014 |
| CN | 104138658 A | 11/2014 |
| CN | 203914881 U | 11/2014 |
| CN | 203934734 U | 11/2014 |
| CN | 204117311 U | 1/2015 |
| CN | 204582326 U | 8/2015 |
| DE | 2113900 A1 | 9/1972 |
| EP | 522882 A2 | 1/1993 |
| EP | 0700270 A1 | 3/1996 |
| EP | 1265825 A2 | 12/2002 |
| EP | 2277691 A1 | 1/2011 |
| EP | 2330937 A2 | 6/2011 |
| EP | 2078477 B1 | 7/2011 |
| EP | 2523231 A1 | 11/2012 |
| EP | 2608287 A1 | 6/2013 |
| EP | 2848139 A1 | 3/2015 |
| EP | 2973766 A1 | 1/2016 |
| JP | 50-114281 U | 2/1974 |
| JP | 05-296861 A | 11/1993 |
| JP | 2002-047370 A | 2/2002 |
| JP | 2002-340700 A | 11/2002 |
| JP | 2002-357487 A | 12/2002 |
| JP | 2003-282983 A | 10/2003 |
| JP | 2006084354 A | 3/2006 |
| JP | 2006-528366 A | 12/2006 |
| JP | 3968430 B2 | 8/2007 |
| JP | 2007-533109 A | 11/2007 |
| JP | 4063564 B2 | 3/2008 |
| JP | 2008-542691 A | 11/2008 |
| JP | 2008-544218 A | 12/2008 |
| JP | 2009-139329 A | 6/2009 |
| JP | 4565109 B2 | 10/2010 |
| JP | 2012-164735 A | 8/2012 |
| JP | 5198608 B2 | 5/2013 |
| JP | S5318893 B2 | 10/2013 |
| JP | 5981852 B2 | 8/2016 |
| KR | 1020100122002 A | 11/2010 |
| KR | 1020120099938 A | 9/2012 |
| SU | 1713821 A1 | 2/1992 |
| WO | 89/10166 A1 | 11/1989 |
| WO | 98/29851 A1 | 7/1998 |
| WO | 00/13582 A1 | 3/2000 |
| WO | 2004/070336 A1 | 8/2004 |
| WO | 2005/117030 A9 | 1/2006 |
| WO | 2006/132463 A1 | 12/2006 |
| WO | 2009/089406 A2 | 7/2009 |
| WO | 2009/108334 A2 | 9/2009 |
| WO | 2010/091258 A1 | 8/2010 |
| WO | 2010/096691 A2 | 8/2010 |
| WO | 2010/131820 A1 | 11/2010 |
| WO | 2011/083611 A1 | 7/2011 |
| WO | 2012/007855 A1 | 1/2012 |
| WO | 2012/035350 A1 | 3/2012 |
| WO | 2012/098840 A1 | 7/2012 |
| WO | 2013/120398 A1 | 8/2013 |
| WO | 2014/008250 A1 | 1/2014 |
| WO | 2014/080429 A1 | 5/2014 |
| WO | 2014/144532 A1 | 9/2014 |
| WO | 2015/003211 A1 | 1/2015 |

OTHER PUBLICATIONS

Shen et al., "Mechanical Characterization of Short Fiber Reinforced Phenolic Foam", Composites Part A: Applied Science and Manufacturing, vol. 34, No. 9, 2003, pp. 899-906.

Han et al., "Thermal Conductivity of Carbon Nanotubes and Their Polymer Nanocomposites: A Review," Progress in Polymer Science, vol. 36, 2011, pp. 914-944.

Saha et al., "Effect of Nanoparticles on Mode-I Fracture Toughness of Polyurethane Foams", Polymer Composites, vol. 30, No. 8, 2009, pp. 1058-1064.

Rizvi et al., "Characterization of a Porous Multifunctional Nanocomposite for Pressure Sensing", ASME 2012 Conference on Smart Materials, Adaptive Structures and Intelligent Systems, American Society of Mechanical Engineers, Abstract, 2012.

M. Taghavi et al., "A Novel Soft Metal-Polymer Composite for Multidirectional Pressure Energy Harvesting," Advanced Energy Materials, vol. 4, May 2, 2014, 6 pages.

Notice of Allowance for Japanese Application No. 2017-093823, dated Mar. 13, 2018, 3 pages.

Office Action with English Translation for Russian Application No. 2015143715, dated Feb. 16, 2018, 12 pages.

S. Bauer, "Piezo-, pyro- and Ferroelectrets: Soft Transducer Materials for Electromechanical Energy Conversion," IEEE Transactions on Dielectrics and Electrical Insulation, vol. 13, No. 5, pp. 953-962, Oct. 2006.

International Search Report and Written Opinion for PCT Application PCT/US2016/012549, dated Mar. 11, 2016, 16 pages.

Alonso et al., "Short-Fiber-Reinforced Epoxy Foams", Composites Part A: Applied Science and Manufacturing, vol. 37, No. 11, 2006, pp. 1952-1960.

Bonato, "Wearable Sensors/Systems and Their Impact on Biomedical Engineering", IEEE Engineering in Medicine and Biology Magazine, May/Jun. 2003, pp. 18-20.

Brady et al., "Inherently Conducting Polymer Modified Polyurethane Smart Foam for Pressure Sensing", Sensors and Actuators A: Physical, vol. 119, 2005, pp. 398-404.

(56) References Cited

OTHER PUBLICATIONS

Calkins, et al., "Applications for a Nano-Composite High Displacement Strain Gauge", 2010, 9 pages.
Calkins, "Nanocomposite High Displacement Strain Gauges for use in Human-Machine Interfaces: Applications in Hand Pose Determination", 2011, 97 pages.
Cannata et al., "An Embedded Artificial Skin for Humanoid Robots", Proceedings of IEEE International Conference on Multisensor Fusion and Integration for Intelligent Systems Seoul, Korea,, Aug. 2008, pp. 434-438.
Challagulla et al., "Electromechanical Response of Piezoelectric foams", Acta Materialia, vol. 60, No. 5, Mar. 2012, pp. 2111-2127.
Chen et al., "Polymer Nanocomposite Foams", Journal of Materials Chemistry A, 2013, pp. 3837-3850.
Cheung et al., "A novel Fluidic Strain Sensor for Large Strain Measurement", Sensors and Actuators A, vol. 147, 2008, pp. 401-408.
Converse et al., "Quantification of Nickel Nanstrand Distributions within a Silicone Matrix using a FIB/SEM System", 2010, 15 pages.
Dai et al., "Electrical Properties of an Ultralight Conductive Carbon Nanotube/Polymer Composite Foam Upon Compression", Polymer-Plastics Technology and Engineering, vol. 51, No. 3, 2012, pp. 304-306.
Flandin et al., "Effect of Strain on the Properties of an Ethylene-Octene Elastomer with Conductive Carbon Fillers", Journal of Applied Polymer Science, vol. 76, 2000, pp. 894-905.
Fleming et al., "In Vivo Measurement of Ligament/Tendon Strains and Forces: A Review", Annals of Biomedical Engineering, vol. 32, No. 3, Mar. 2004, pp. 318-328.
Fullwood et al., "Dispersion Metrics for Composites—a Machine Learning Based Analysis", SAMPE International. Long Beach, CA, 2013, 12 pages.
Gerhard-Multhaupt, "Less can be More: Holes in Polymers Lead to a New Paradigm of Piezoelectric Materials for Electret Transducers", IEEE transactions on Diaelectrics and Electrical Insulation, vol. 9 No. 5, Oct. 2002, pp. 850-859.
Hampshire et al., "Monitoring the Behavior of Steel Structures Using Distributed Optical Fiber Sensors", Journal of Constructional Steel Research, vol. 53, 2000, pp. 267-281.
Hyatt et al., "Nano-composite Sensors for Wide Range Measurement of Ligament Strain", Proceedings of the SEM Annual Conference, Society of Experimental Mechanics Inc., Jun. 2010, 4 pages.
Ibeh et al., "Current trends in nanocomposite foams", Journal of Cellular Plastics, vol. 44, No. 6, 2008, pp. 493-515.
Johnson et al., "A Percolation/Quantum Tunneling Model for the Unique Behavior of Multifunctional Silicon/Nickel Nanostrand Nanocomposites", Society for the Advancement of Material and Process Engineering, 2010, 10 pages.
Johnson et al., "Multiscale Model for the Extreme Piezoresistivity in Silicon/Nickel Nanostrand Nanocomposites", 2011, 11 pages.
Johnson et al., "Nanocomposite Large-Strain Sensor Optimization", 2009, 1 page.
Johnson et al., "Optimization of Nickel Nanocomposite for Large Strain Sensing Applications", Sensors and Actuators A, vol. 166, 2011, pp. 40-47.
Johnson et al., "The Colossal Piezoresistive Effect in Nickel Nanostrand Polymer Composites and a Quantum Tunneling Model", Tech Science Press, CMC, vol. 15, No. 2, 2010, pp. 87-111.
Kanda, "High Strain Electrostrictive Polymers: Elaboration Methods and Modelization", URL:https://tel.archives-ouvertes.fr/tel-00701539/document, May 25, 2012, 164 pages.
Koecher et al., "Characterization of Nickel Nanostrand Nanocomposites through Dielectric Spectroscopy and Nanoindentation", Polymer Engineering & Science, Apr. 2, 2013, pp. 2666-2673.
Lindner et al., "Dielectric Barrier Microdischarges: Mechanism for the Charging of Cellular Piezoelectric Polymers", Journal of Applied Physics, vol. 91, No. 8,, Apr. 15, 2002, pp. 5283-5287.
Ma et al., "The Effect of Surface Chemistry of Graphene on Cellular Structures and Electrical Properties of Polycarbonate Nanocomposite Foams", Industrial & Engineering Chemistry Research, vol. 53, No. 12, 2014, pp. 4697-4703.
Mahfuz et al., "Fabrication, Synthesis and Mechanical Characterization of Nanoparticles Infused Polyurethane Foams", Composites Part A: Applied Science and Manufacturing, vol. 35, No. 4, 2004, pp. 453-460.
Merrell et al., "Applications of Nano-Composite Piezoelectric Foam Sensors", Proceedings of ASME conference on Smart Materials. SMASIS. Salt Lake City, Sep. 16-18, 2013, 5 pages.
Neugschwandtner et al., "Large and Broadband Piezoelectricity in Smart Polymer-Foam Space-Charge Electrets", Applied Physics Letters, vol. 77, No. 23, Dec. 4, 2000, pp. 3827-3829.
Patel, "Ceramic Based Intelligent Piezoelectric Energy Harvesting Device", Ch. 8 of the book "Advances in Ceramics—Electric and Magnetic Ceramics, Bioceramics, Ceramics and Environement" published on Sep. 6, 2011, pp. 133-154.
Patel et al., "Longitudinal Monitoring of Patients with Parkinson's Disease via Wearable Sensor Technology in the Home Setting", 33rd Annual International Conference of the IEEE EMBS Boston, Massachusetts USA, Aug. 30-Sep. 3, 2011, pp. 1552-1555.
Remington et al., "Biomechanical Applications of Quantum Nano-Composite Strain Gauges", Brigham Young University, Provo, 2013, pp. 1-4.
Tao et al., "Gait Analysis Using Wearable Sensors", Sensors 2012, vol. 12, 2012, pp. 2255-2283.
Ventrelli et al., "Development of a stretchable skin-like tactile sensor based on polymeric composites", Proceedings of the 2009 IEEE International Conference on Robotics and Biomimetics, Dec. 19-23, 2009, pp. 123-128.
Verdejo et al., "Enhanced acoustic damping in flexible polyurethane foams filled with carbon nanotubes", Composites Science and Technology 69.10, (2009), pp. 1564-1569.
Verdejo et al., "Physical properties of silicone foams filled with carbon nanotubes and functionalized graphene sheets", European Polymer Journal 44.9, (2008), pp. 2790-2797.
Wang, "Piezoelectric Nanogenerators for Self-Powered Nanosensors and Nanosystems", Wang, "Piezoelectric Nanogenerators for Self-Powered Nanosensors and Nanosystems", Wiley Encyclopedia of Electrical and Electronics Engineering, 2012, 20 pages.
Watanabe et al., "Tests of Wireless Wearable Sensor System in Joint Angle Measurement of Lower Limbs", 33rd Annual International Conference of the IEEE EMBS Boston, Massachusetts USA, Aug. 30-Sep. 3, 2011, pp. 5469-5472.
Wegener, "Piezoelectric polymer foams: transducer mechanism and preparation as well as touch-sensor and ultrasonic-transducer properties", 2010, pp. 1-9.
Yan et al., "Electrical Conductivity and Major Mechanical and Thermal Properties of Carbon Nanotube-Filled Polyurethane Foams", Journal of Applied polymer Science, vol. 120, No. 5, 2011, pp. 3014-3019.
Yang et al., "Conductive Carbon Nanofiber-Polymer Foam Structures", Advanced Materials, vol. 17, No. 16, 2005, pp. 1999-2003.
Yao et al., "Wearable Multifunctional Sensors Using Printed Stretchable Conductors Made of Silver Nanowires", © The Royal Society of Chemistry, Dec. 5, 2013, 8 pages.
Zeng et al., "Synthesis and Processing of PMMA Carbon Nanotube Nanocomposite Foams", Polymer, vol. 51, No. 3, Jan. 4, 2010, pp. 655-664.

\* cited by examiner

SHOE-BASED ANALYSIS SYSTEM

RELATED APPLICATION

This application is a continuation of, and claims priority to, U.S. patent application Ser. No. 14/990,763, filed on Jan. 7, 2016, which is a non-provisional of, and claims priority to, U.S. Provisional Application No. 62/100,851, titled SHOE-BASED ANALYSIS SYSTEM, filed Jan. 7, 2015, the disclosures of which are incorporated herein by reference in their entireties.

FEDERALLY SPONSORED RESEARCH

This application was made with support from a government grant under Grant Number NSF CMMI-1538447 awarded by the National Science Foundation. The government has certain rights in this application.

BACKGROUND

In physical activity good form is essential to the comfort and health of the participants. Through gait analysis one can determine how the foot is coming into contact with the various surfaces. This information can be used to determine, for example, a runner's form, but highly accurate gait analysis is currently expensive to perform and limited to a laboratory setting.

SUMMARY

The apparatus and methods described herein related to a self-sensing composite polymeric foam are configured to determine various types of data related to how one's foot comes into contact with a surface, such as the ground, a pedal, a ball, a wall, a beam, etc. A self-sensing composite polymeric foam produces electrical data, either in the form of a change in resistance or in the form of a voltage, when compressed. In some implementations, a portion of the existing foam in the shoe is replaced with a self-sensing composite polymeric foam. In other words, the self-sensing composite polymeric foam functions as a portion of the shoe. Put another way, the self-sensing composite polymeric foam has dual functions, one as a sensor and another as padding or support. This dual-function makes the self-sensing composite polymeric foam a non-additive sensor. The composite polymeric foam may be shaped as the portion of the shoe it replaces, added as a long continuous piece, and/or provided at one or more discrete locations. The different configurations can create or implement a variety of strain and impact sensing capabilities, e.g., weight detection, ground reaction force, pressure, acceleration. The configurations can be adjusted for a variety of activities (e.g., biking, running, or kicking a ball). In some implementations, the voltage data generated by the self-sensing polymeric foam is compared to a profile, and the wearer is provided with physical feedback in real time to correct gait, weight transfer, or other differences with the profile data. In some implementations, the self-sensing composite polymeric foam is also thermally conductive. In some implementations the self-sensing composite polymeric foam offers optimized stiffness and damping capabilities.

In one general aspect, an apparatus includes a shoe having a sole, the sole having at least a portion of foam replaced with a self-sensing composite polymeric foam, at least one probe disposed in the self-sensing composite polymeric foam, a voltage detector coupled to the probe that detects voltage data generated by the self-sensing composite polymeric foam, and a transformation module that converts voltage data generated by the self-sensing composite polymeric foam in response to deformation events into ground reaction force data.

In one general aspect, an apparatus includes a shoe having a sole, the sole having an insert that includes self-sensing composite polymeric foam, a plurality of probes disposed in the self-sensing composite polymeric foam, at least one voltage detector coupled to the plurality of probes that detects voltage data generated by the self-sensing composite polymeric foam, and a transformation module that converts voltage data generated by the self-sensing composite polymeric foam in response to deformation events into ground reaction force data.

In one general aspect, a method includes receiving voltage data produced by a self-sensing composite polymeric foam, the self-sensing composite polymeric foam providing support and padding in the sole of a shoe, converting the voltage data to force data, comparing the force data to a profile, and transmitting, when the force data fails to fall within a threshold of the profile, a feedback signal to a physical feedback device, the feedback signal indicating a difference with the profile.

In one general aspect, an apparatus, comprises a shoe having foam-based padding, wherein at least a portion of foam-based padding is replaced with a self-sensing composite polymeric foam, at least one probe disposed in the self-sensing composite polymeric foam, a voltage detector coupled to the probe that detects voltage data generated by the self-sensing composite polymeric foam, and a transformation module that converts voltage data generated by the self-sensing composite polymeric foam in response to an impact event into pressure data.

In one general aspect, a shoe insert comprises self-sensing composite polymeric foam, a plurality of probes disposed in the composite polymeric foam, at least one voltage detector coupled to the plurality of probes, the voltage detector configured to detect voltage data generated by the self-sensing composite polymeric foam, and a microcontroller configured to store the voltage data.

One or more of the implementations of the subject matter described herein can be implemented so as to realize one or more of the following advantages. For example, implementations provide highly accurate data regarding gait, ground reaction force, pressure, and acceleration. The data provided by the composite polymeric foam correlates highly to data conventionally available only in a laboratory setting. Thus the data is highly accurate. Such data can be used to determine that the shoe wearer is fatigued, has received a concussion or other injury and even to identify the wearer as depressed. As another example, implementations can provide real-time feedback for correcting gait, weight transfer, etc., so that the person wearing the shoe is made aware of such errors. For example, the shoe-based analysis system may include one or more profiles of ideal or desired activity patterns and the voltage data provided by the self-sensing composite polymeric foam can be compared against an activity profile. When the shoe-based analysis system identifies a difference with the profile, the shoe-based analysis system can provide physical feedback, e.g., in the form of vibrations, lights, sounds, images, or a message, that alerts the wearer of the error. In some implementations, the physical feedback may indicate a specific difference, such as improper acceleration, an improper foot strike, including improper pronation, heel strike, etc. As another benefit, the composite polymeric foam is more thermally conductive than non-sensing foams and reduces hotspots when it replaces the existing foam in parts of a shoe. Hotspots lead to worse injuries such as tendonitis, runner's knee, and plantar fasciitis, etc. Some of these injuries occur when a runner changes gait to alleviate a hot spot. Thus, implementations not only allow an athlete of any skill level to run longer and run cooler and continue with their normal gait pattern and not have to alter it because of a hotspot, but can also notify the athlete when a change in gait is detected.

DETAILED DESCRIPTION

Figure 1:
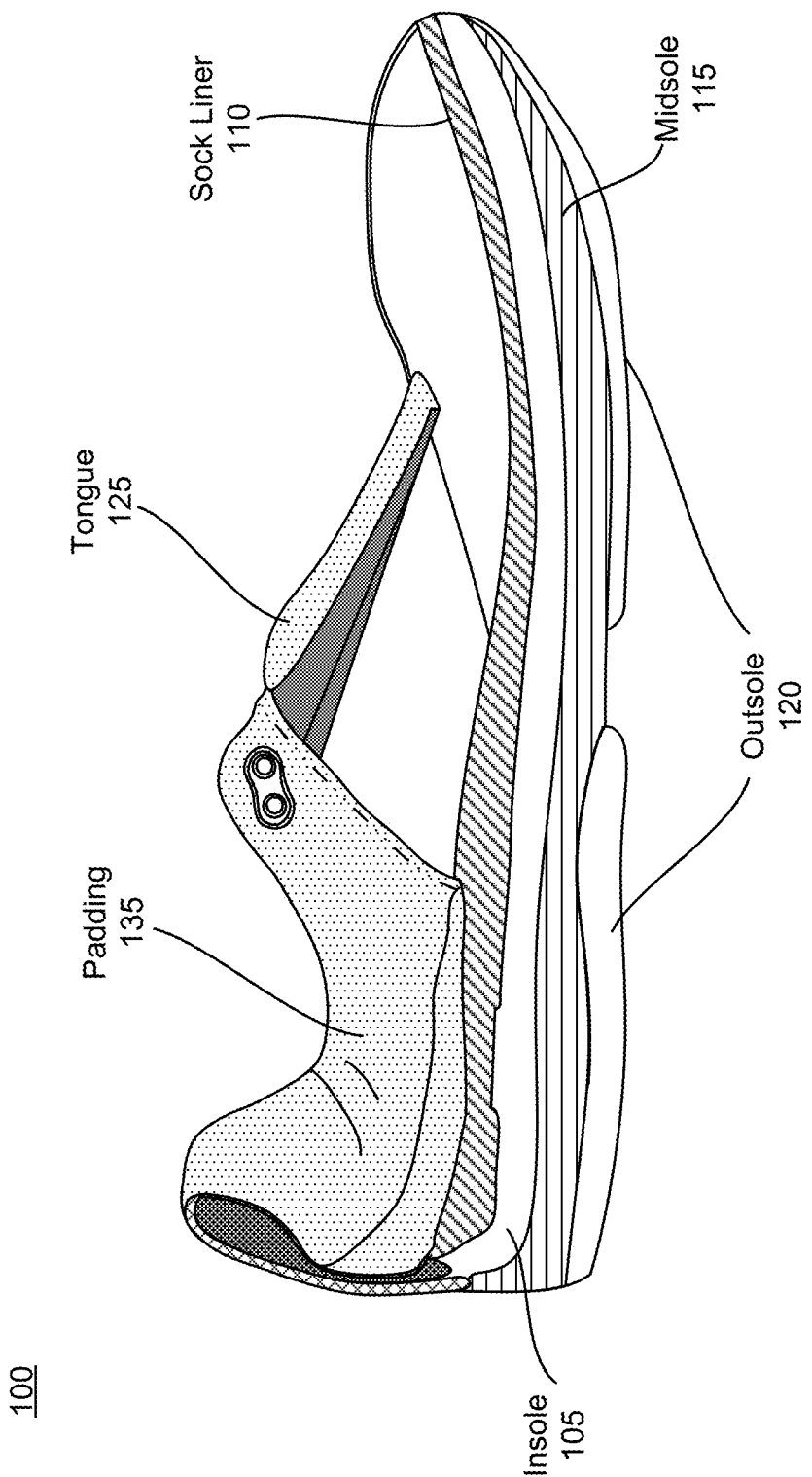
FIG. 1 is a cross-section that illustrates parts of a shoe-based analysis system.

FIG. 1 is a cross-section that illustrates various parts of a typical athletic shoe. For example, the bottom or sole of the shoe includes an outsole 120 that comes in direct contact with the ground. The outsole is conventionally made of leather, resin rubber, natural rubber, or a foam type of material. Foam outsoles are used in many athletic shoes. The sole also includes a midsole 115 that provides cushioning and pronation control. The midsole 115 is conventionally made of foam materials that provide comfort. The sole also includes an insole board 105. The insole 105 can be made of cellulosic paper board or foam materials and can provide comfort and/or support. A shoe may also include a sock liner 110. When a shoe includes a sock liner, the sock liner 110 may be in direct contact with the foot or socks of the wearer and is sometimes designed to wick away moisture and provide additional cushioning. In some shoes the sock liner can be covered by another insole (e.g., an inserted insole). In a shoe without a sock liner, the insole 105 is in direct contact with the foot or socks of the wearer. A shoe 100 can also include a tongue 130. The tongue 130 provides cushioning at the top of the wearer's foot under the laces. Finally, the shoe may also include other areas of padding 135, such as at the sides or back of the shoe. The padding 135 may be covered by a lining.

In the shoe-based analysis system, a self-sensing composite polymer foam replaces all of, or portions of, the shoe that provide padding. For example, the self-sensing composite polymer foam may replace all of or portions of the tongue 125, the padding 135, and/or the sock liner 110, the insole 105, the midsole 115, or the outsole 120 of a shoe 100. The self-sensing composite polymer foam may be non-additive in that the foam performs two functions simultaneously: as a sensor and as padding and/or support. For instance, all of or a portion of the foam already present in the shoe may be removed and replaced with the self-sensing composite polymer foam. Moreover, in some implementations, the self-sensing composite polymeric foam may have a modulus or Young's modulus that matches that of the removed foam to provide the same support factor or damping as the existing foam. In some implementations, the self-sensing composite polymer foam may be an insole or orthotic that is later inserted into the shoe. Such a later-added insole is still non-additive as it functions as padding/support and a sensor. Thus, the composite polymeric foam mimics the physical properties of existing materials in the shoe and wearers of the shoe do not notice a difference between the shoe-based analysis system and a regular shoe that lacks the sensors.

The self-sensing composite polymeric foam is a sensor because the self-sensing composite polymer foam is able to generate or modify an electrical signal (e.g. generating a voltage, or changing resistance) that can be measured when deformed. In this sense the composite polymer foam is strain-sensitive and or impact-sensitive. The self-sensing composite polymer may be a foam that generates a voltage (e.g., an electrical charge) when impacted and/or causes a change in resistance upon deformation. In other words, the self-sensing polymeric foam can both produce both resistive and electric voltage data simultaneously. In some implementations the change in resistance may be used to measure strain and the electric voltage data may be used to measure impact (e.g., strain rate and total strain). The electrical data, whether an electric voltage, resistance data, or both, that the self-sensing composite polymeric foam produces upon deformation can then be analyzed to determine one or more sequences or patterns of impact, the magnitude of impact, ground reaction force, the weight of the user, acceleration, pressure, and/or so forth. This information can then be used and/or processed to train the runner on desirable running form, track caloric output, train on proper kicking, and/or so forth. These mechanisms included in one or more shoes could also be used in physical rehabilitation, medical gait analysis, and/or so forth.

Figure 2A:
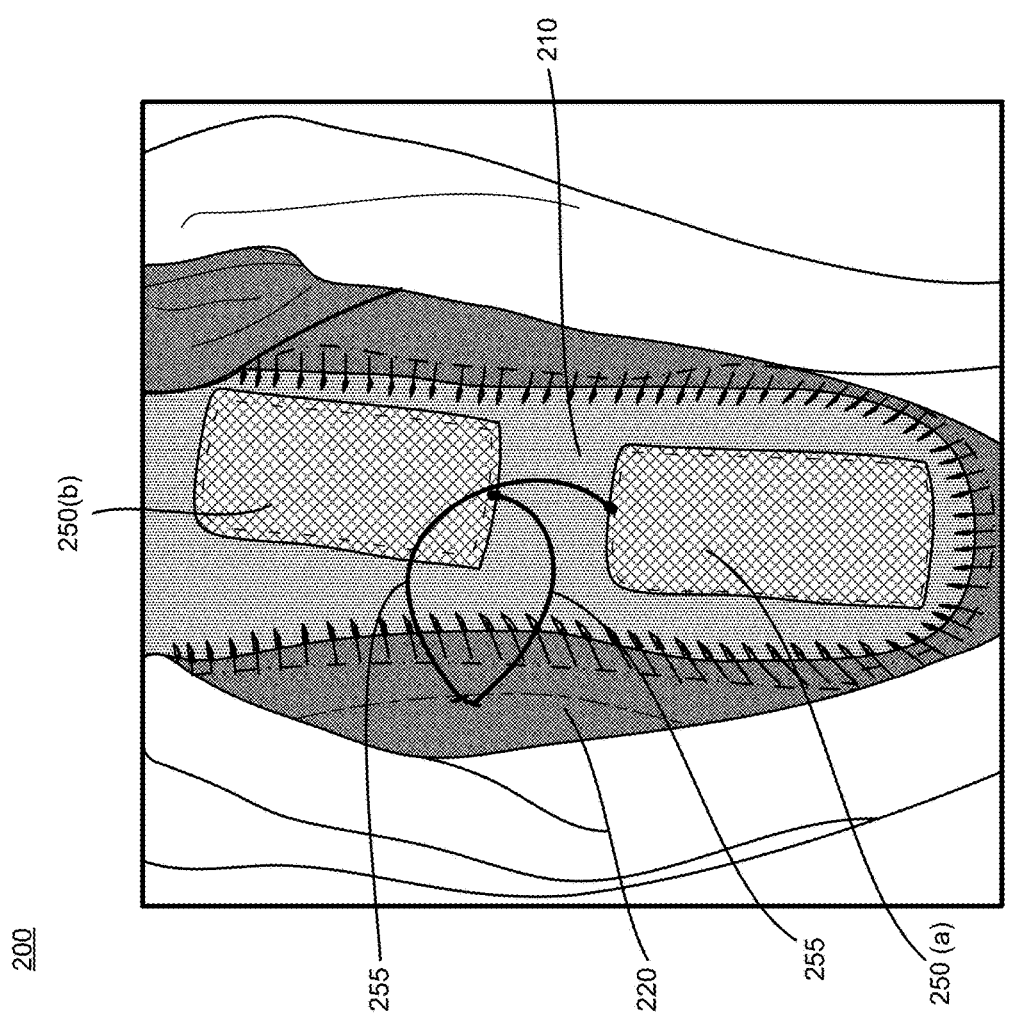
FIGS. 2A to 2B are diagrams illustrating example placement of sensors in a shoe-based analysis system, according to an implementation.
Figure 2B:
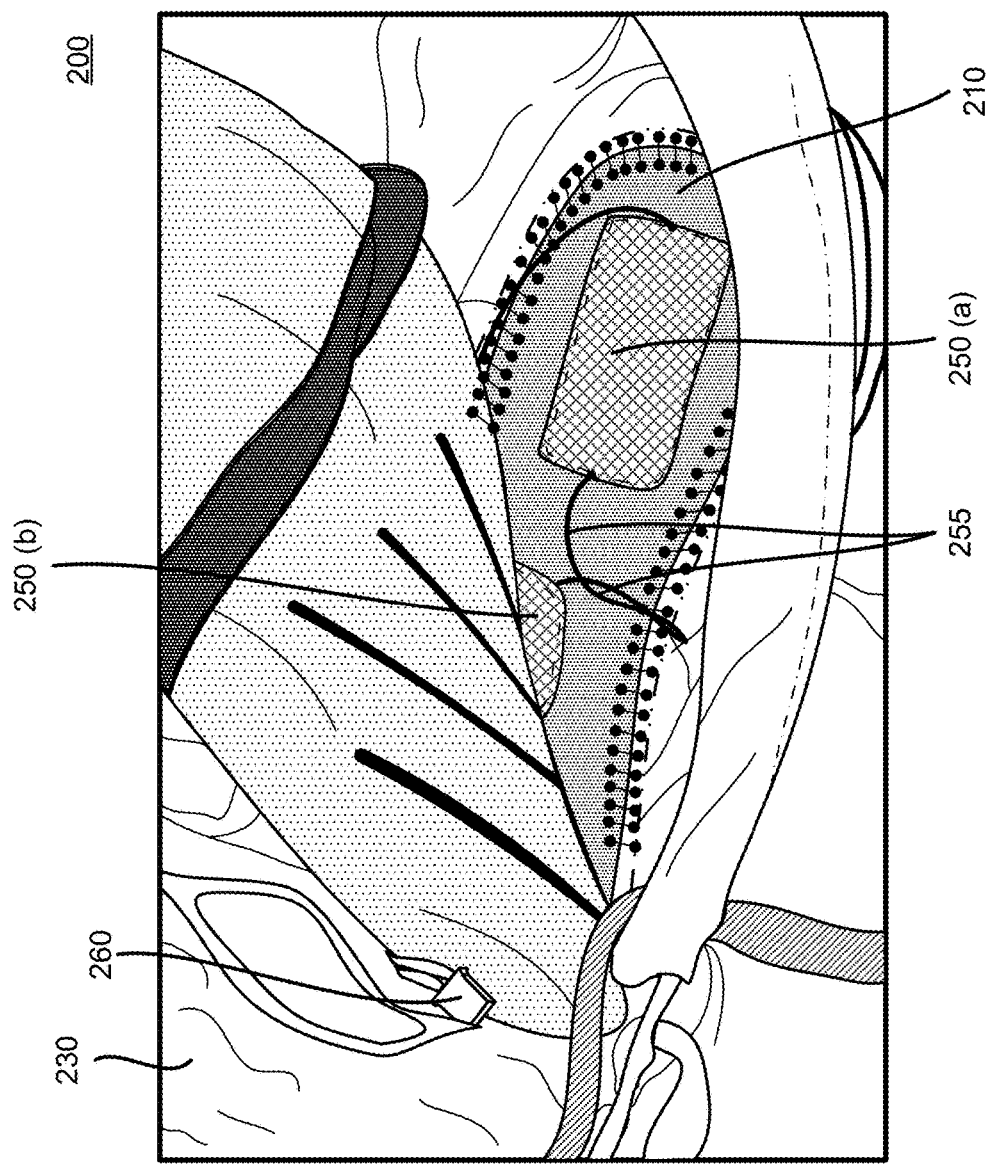

FIG. 2A to FIG. 2B are diagrams that illustrate example placement of sensors in a shoe-based analysis system, according to an embodiment. In the example of FIG. 2A, portions of the sock liner 210 have been removed and replaced with self-sensing composite polymeric foam sensors 250(a) and 250(b). Accordingly, the two sensors 250(a) and 250(b) also function as the sock liner 210, or are included as a part of the sock liner 210. Each sensor 250(a) and 250(b) constitutes a separate sensor that can produce voltage data, in the form of voltage or a change in resistance. The shoe 200 may also include additional sensors 250, e.g., at a position corresponding to the ball, toe, and/or arch of the foot, that are not illustrated in FIG. 2A. One or more of the sensors 250(a) and 250(b) that replace portions of the shoe (e.g., the sock liner 210 or insole 205) can have one or more probes 255 inserted into the sensor that connect the sensors 250(a) and 250(b) to one or more microcontrollers. The probes 255 may be a pair of wires made of any conductive material. The microcontrollers are configured to monitor, for example, voltage or another electrical property such as resistance. In the example of FIG. 2A, foam in the sock liner 210 was removed and replaced with foam sensors 250(a) and 250(b) as described herein. While FIG. 2A illustrates replacement of portions of the sock liner 210, sensors 250(a) and 250(b) may also replace portions of the insole 105, the midsole 115 or the outsole 120. In addition, the sensors, or in other words the self-sensing polymeric foam, may be shaped to replace other padded areas, such as padding 135 and/or tongue 125.

The probes 255 (which can include, for example, a wire, a contact, etc.) are coupled to (e.g., run between) the sensors 250 and a microcontroller, such as microcontroller 260 illustrated in FIG. 2B. In some implementations, the probes 255 may run between the lining of the shoe 200 and the outside of the shoe 200 to the tongue 230 where the microcontroller 260 is placed to monitor the voltage data from all of the sensors. The microcontroller 260 could also be placed elsewhere, for example, in the heel of the shoe 200 or the padding of the shoe 200. Each sensor, e.g., the self-sensing composite polymeric foam, is capable of producing both a piezoelectric and a piezoresistive response. In other words, the microcontroller 260 can measure both resistive and electric voltage data from each sensor. Although not illustrated in FIG. 2B, the foam padding of the tongue 230 may be replaced with self-sensing polymeric foam as another sensor 250. When the self-sensing polymeric foam 250 replaces the foam in the tongue 230, the energy that is transmitted to a ball when kicked could be determined. Although not illustrated in FIG. 2A or 2B, the composite polymeric foam could also be placed in the midsole 115 with the sock liner 110 and/or insole 105 covering it to add a level of element separation between the foot of the wearer and the sensor 250 to increase reliability of the sensors 250. FIGS. 2A and 2B are presented by way of example only. The various components described above could be modified and/or included in different portions of the shoe. For example, the tongue 230 and the sock liner 210 may have their own microcontroller. In some implementations, additional or less microcontrollers, foam sensors, and/or wires could be included or excluded in the shoe-based analysis system.

Figure 3:
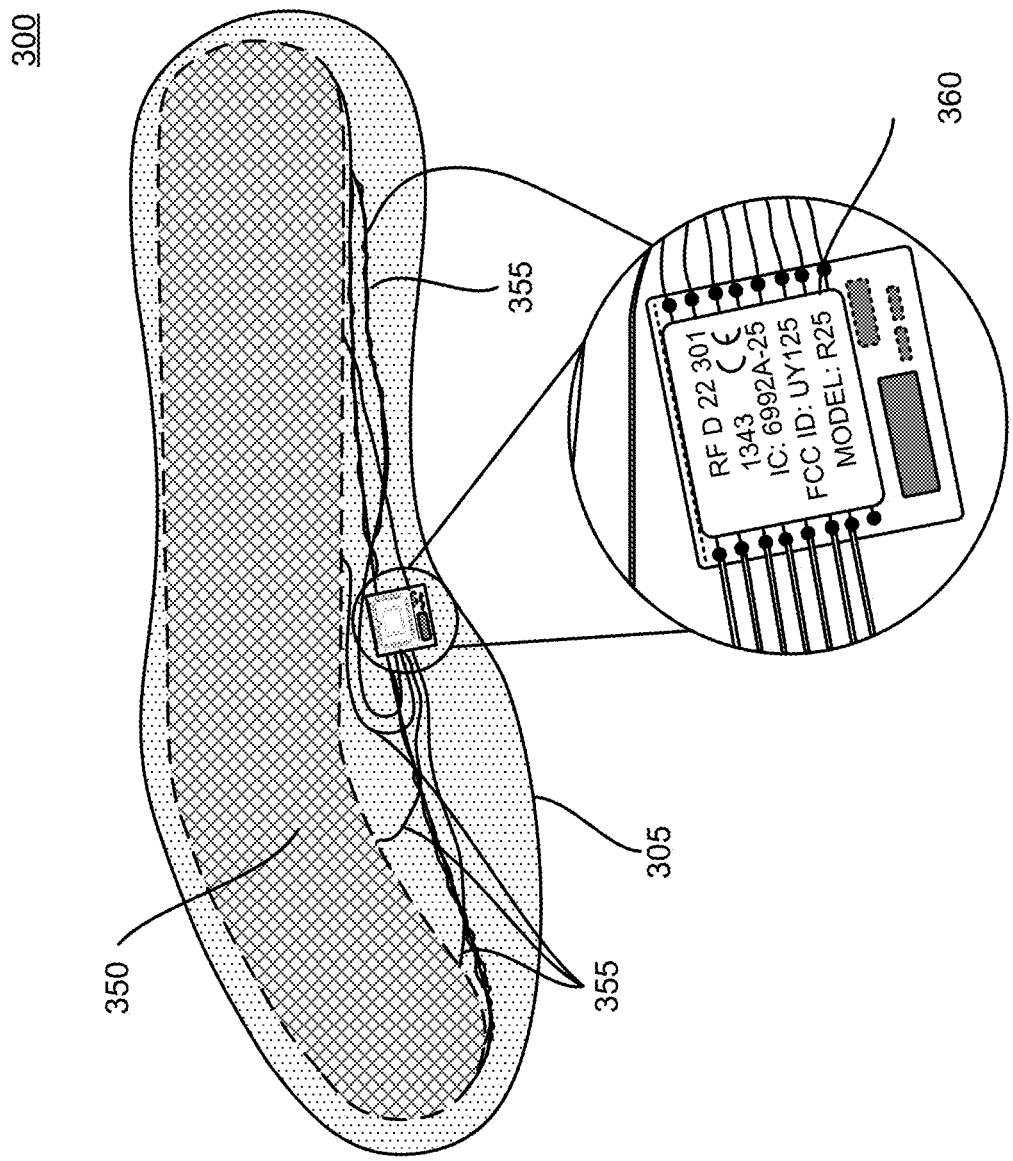
FIG. 3 illustrates another example placement of sensors in a shoe based analysis system, according to an implementation.

FIG. 3 illustrates another example placement of self-sensing composite polymer foam in a shoe based analysis system. In the example of FIG. 3, the sensor 350 (i.e., the self-sensing composite polymer foam) replaces a majority (e.g., greater than 50% in surface area and/or volume) of the insole 305. Thus, the insole 300 is self-contained and may be added to the shoe after purchase, e.g., added by the wearer of the shoe. In some implementations the insole 200 may be included in the shoe as it is manufactured. In either case the insole still functions as padding and/or support for the wearer in addition to functioning as a sensor. In the example of FIG. 3, the microcontroller 360 is included in the insole 305 itself. Probes 355 are inserted into the sensor 350 at locations that measure voltage data corresponding to the toe, ball, inner arch, and heel of the wearer's foot. Thus, the sensor 350 and probes 355 provides four points for voltage data collection. The sensor 350 is capable of generating or producing a voltage, e.g. an electrical charge, in response to deformation in addition to producing a change in resistance in response to deformation. Thus, the four probes 355 may provide eight different sources of data. In some implementations, the sensor 350 may replace the entire insole 305 and the microcontroller 360 may be located elsewhere in the shoe, e.g., the tongue, a sidewall, or another layer of the sole (e.g., the midsole or wedge).

Figure 4A:
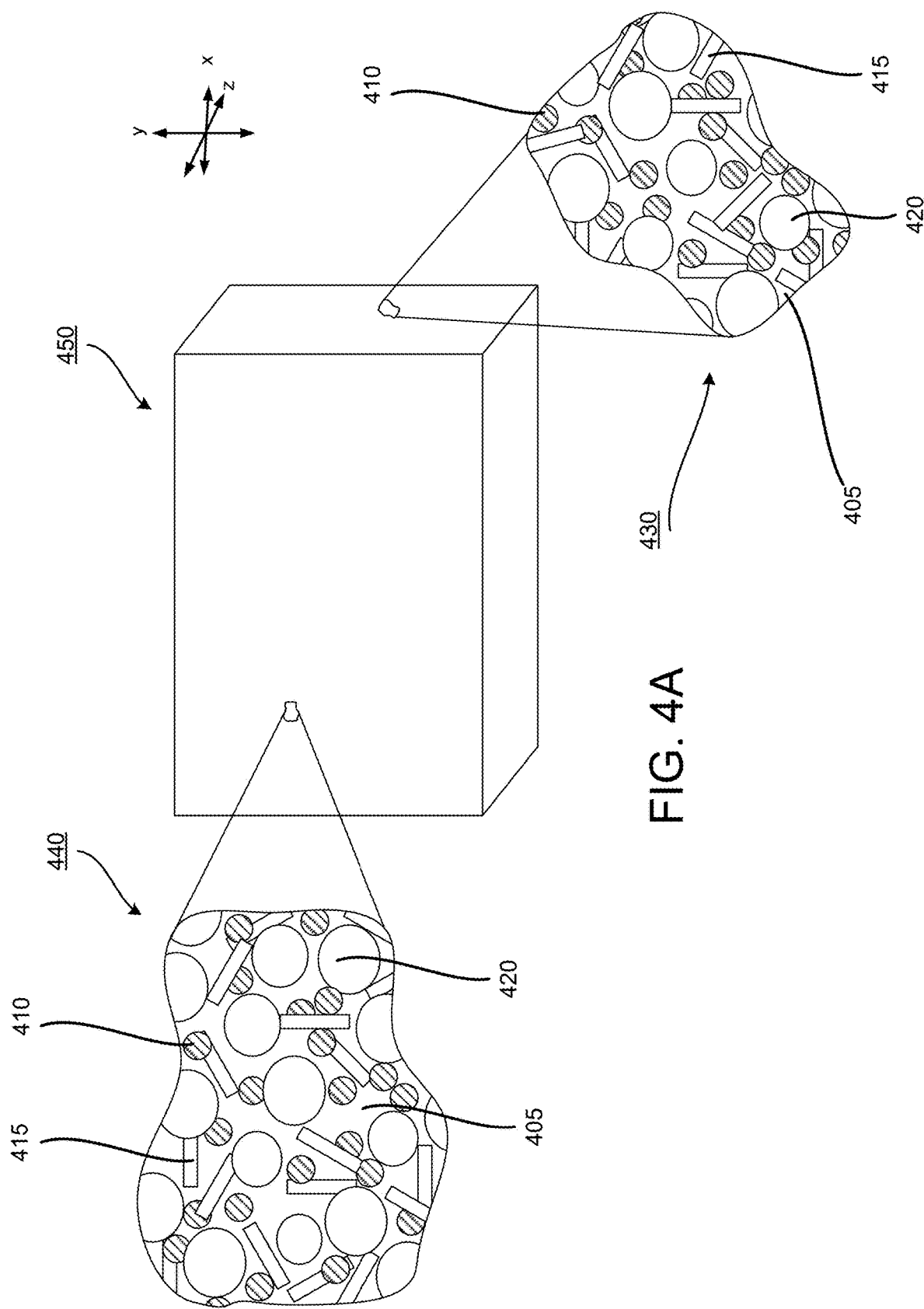
FIGS. 4A to 4C are block diagrams illustrating an example strain-sensing composite polymer, according to an implementation.
Figure 4B:
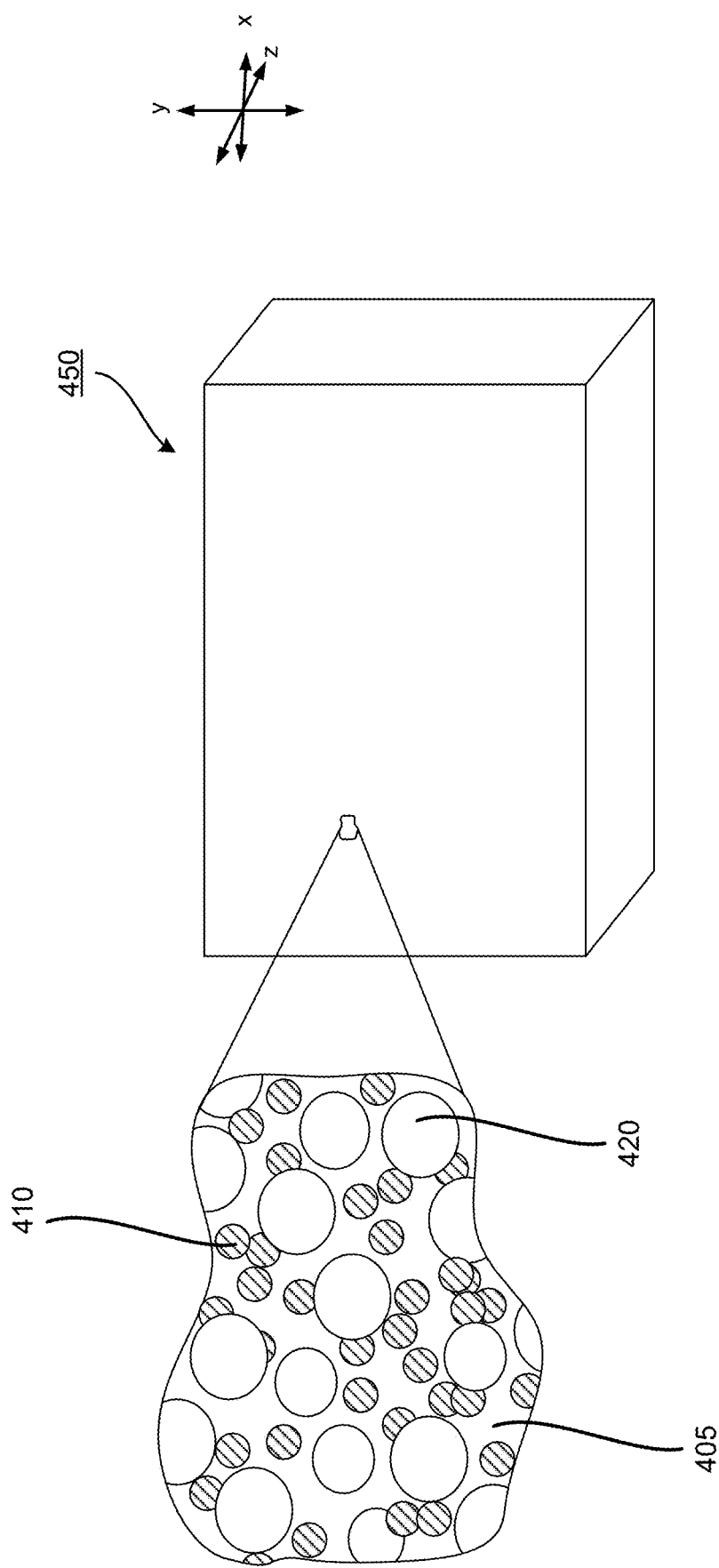
Figure 4C:
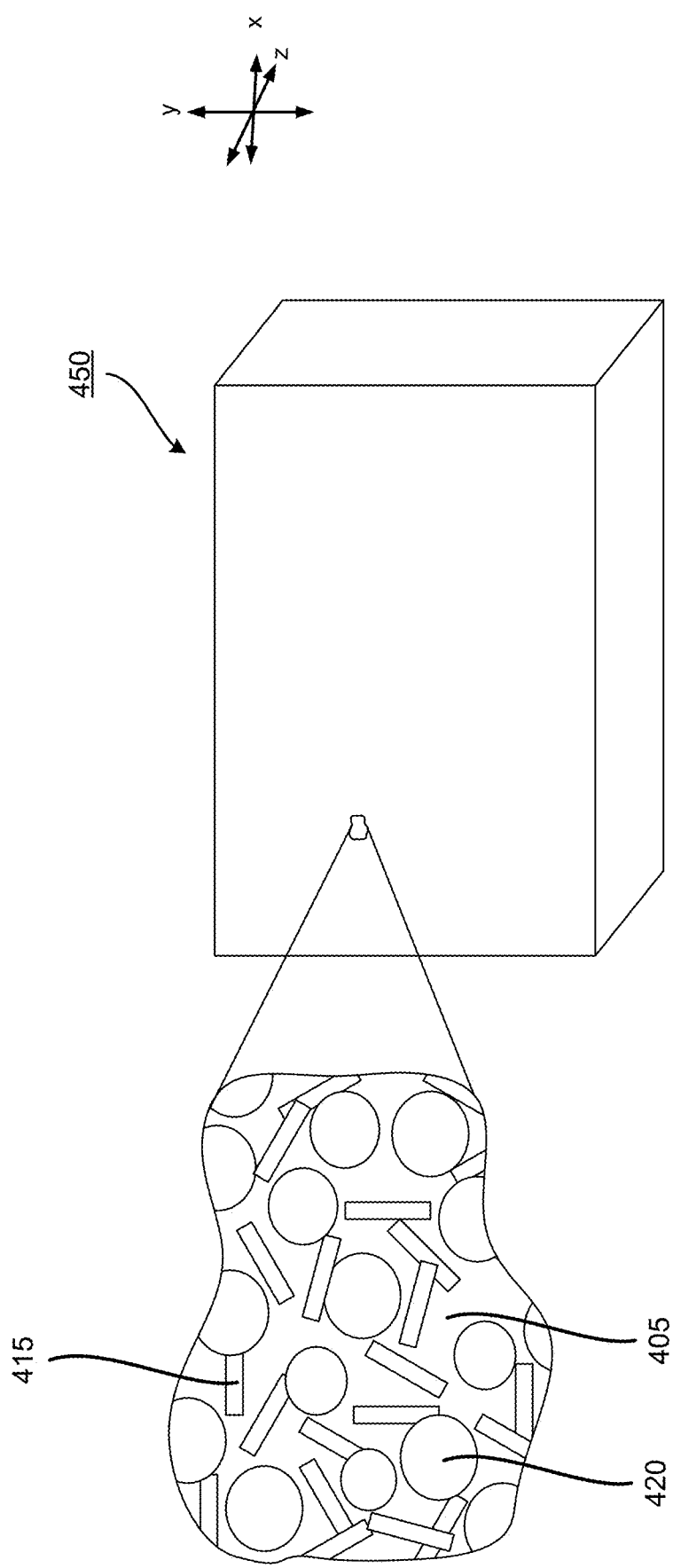

FIGS. 4A to 4C are block diagrams illustrating an example strain-sensing composite polymer foam 450, according to an implementation. The composite polymer foam 450 can be used as a sensor, e.g., sensors 250(a) and 250(b) of FIG. 2A or sensor 350 of FIG. 3. FIG. 4A is a high-level schematic diagram of a self-sensing composite polymeric foam 450 that exhibits a piezoelectric response and a negative piezoresistive effect to deformation, e.g., compression and relaxation, according to one implementation. The composite polymeric foam 450 also exhibits a piezoelectric response and/or piezoresistivity in response to tensile strain. The composite polymeric foam 450 may include several components: a matrix 405 with one or more conductive fillers (e.g., conductive nanoparticles 410, conductive stabilizers 415), and voids 420. The voids 420 and conductive fillers may be uniformly dispersed throughout the matrix. The matrix 405 may be any polymer, such as a silicone-based material, an elastomer, a polyurethane material, EVA (ethylvinyl acetate), polyethylene, SBR (styrene butadiene rubber), neoprene, latex, or other foam-like material, etc., that retains its shape after deformation and includes voids 420 throughout the material. In other words, the matrix 405 is comprised of material that has elasticity, porosity, and high failure strain, typically from 50% to 1000% strain.

In some implementations, the polymer matrix 405 may be a foam-based product that forms voids 420, for example through a chemical reaction, introduction of a foaming agent, through gas injection, etc. The voids 420 may give the composite polymeric foam 450 relatively low weight, relatively low density, and relatively high energy absorption. In other words, unlike a solid material, in composite polymeric foam 450 the voids 420 are dispersed throughout the matrix 405. For example, the density of the polymer used for matrix 405 may be approximately two to forty times greater without the voids than with the voids. For example, in some implementations the composite polymeric foam 450 may have a density from 30 kg/m$^3$ to 800 kg/m$^3$.

The composite polymeric foam 450 may also have porosity due to the voids 420. The porosity of the composite polymeric foam 450 may be defined in terms of the volume fraction of air and the size of the voids 420. Each of these elements may be affected by several factors, including the polymer used as the matrix 405, the process used to form the voids 420, confinement of the composite polymeric foam 450 during formation of the voids and/or curing (e.g., size and shape of a mold and amount of composite material introduced into the mold), and the amount and type of the conductive fillers mixed with the polymer, etc. For example, inclusion of conductive nanoparticles 410 tends to decrease the size of the voids 420. Voids may be open-cell (e.g., the voids may run into or connect with each other) or closed-cell (e.g., the voids are separate from each other) and can vary in size depending on a number of factors. In some implementations the voids 420 may range in size up to 1000 µm.

In some implementations, the polymer used as the matrix 405 may be capable of being mixed with conductive fillers prior to curing. For example, some polymeric foams may be thermoset, or irreversibly cured via heat, a chemical reaction, or irradiation. Prior to curing, conductive fillers may be combined with the uncured polymer. For example, a polymer cured via a chemical reaction, such as foam, may include two parts, the polymer foam being formed when the two parts are mixed or combined. Once combined, the two parts chemically react, generating the air pockets or voids characteristic of foam, and harden. Conductive fillers may be mixed with one or both parts prior to combining. Some polymers may be mixed with a foaming agent prior to curing. Such polymeric foams may be combined with conductive fillers prior to mixing with the foaming agent. Voids may be formed in the composite polymeric foam by gas injection, by whipping, etc. Some polymers may be cured via heat. Thermoset polymeric foams may be cast, molded, sprayed or extruded after mixing and before they cure. Thus, the composite polymeric foam 450 can be shaped according to the requirements of the portion of the shoe that it replaces.

In some implementations, the conductive filler may include conductive nanoparticles 410. Conductive nanoparticles 410 are particles with at least one dimension that measures 1.5 microns or less and that are also made from a material that conducts electricity. Examples of such conductive materials include nickel, platinum, gold, silver, copper, carbon, (e.g., carbon nanotubes, carbon black, graphite, etc.) etc. Examples of conductive nanoparticles 410 include nanowires, powders, and nanostrands. Examples of nanostrands that can be included is a nickel nanostrand (NiN) and Novamet 525. NiNs are available from Conductive Composites, LLC (Heber City, Utah) and are described by U.S. Pat. No. 7,935,415 entitled "Electrically Conductive Composite Material" and U.S. Pat. No. 8,361,608, entitled "Electrically Conductive Nanocomposite Material," which are incorporated herein by reference. Novamet 525 is manufactured by Vale and marketed as T255 powder.

The conductive filler may also include a plurality of conductive stabilizers 415. The conductive stabilizers 415 may also be added to the uncured polymer prior to formation of the voids. The conductive stabilizers 415 may be any conductive material that acts as a stabilizer. In some implementations the conductive stabilizers 415 may be carbon fibers. In one implementation, the conductive stabilizers 415 may be fibers coated with a material that conducts electricity. For example, the conductive stabilizers 415 may be fibers coated with pure nickel. In some implementations, the fibers may be coated approximately 20-40% by weight with the conductive material. The fibers may be cut to short lengths, for example from 0.1 to 1 mm. The fibers may have a diameter of up to 10 µm (e.g., 0.2 µm, 1 µm, 5 µm, 8 µm). In some implementations, the fibers may be hollow (e.g., tubes). The conductive stabilizers 415 may increase the strength and energy absorption capabilities of the composite polymeric foam 450. The conductive nanoparticles 410 may also increase the strength and energy absorption capabilities of the composite polymeric foam 450, but typically to a lesser extent than the conductive stabilizers 415. In some implementations, the conductive nanoparticles 410 may be a primary conductive filler and the conductive stabilizers 415 may be a secondary conductive filler.

Because the conductive fillers, for example conductive nanoparticles 410 and/or the conductive stabilizers 415, are mixed with, and thus disposed throughout, the polymer matrix 405, the composite polymeric foam 450 is uniform. Put another way, the composite polymeric foam 450, and thus the sensor, does not have layers and its composition is generally consistent at a macroscopic (e.g., naked eye) level from outer surface (outer wall) to outer surface. In some implementations, the composite polymeric foam 450 may also have isotropic properties at a macroscopic level in that it does not exhibit a preferred directionality. For example, the composite polymeric foam 450 may exhibit piezoelectric response or piezoresistivity along the x-axis, the y-axis, and the z-axis, which are illustrated in FIG. 4A. In other words, the composite polymeric foam 450 may exhibit piezoelectric response or piezoresistivity detectable from one outer surface of the material to another outer surface, regardless of which outer surfaces are used. In some implementations the composite polymeric foam 450 may have anisotropic properties. For example, the conductive fillers may be aligned in a particular direction to gain better measurements in that particular direction. Alignment of the conductive fillers can be accomplished through the manufacturing process like extruding the product through a hose. It may also be possible to align the conductive fillers using a magnetic field. As illustrated in FIG. 4A, the conductive nanoparticles 410 and the conductive stabilizers 415 may not be easily visible without magnification, such as magnification areas 430 and 440. At a microscopic level, e.g., illustrated by magnification areas 430 and 440, the components of the composite polymeric foam 450 may be distinguishable, but may be generally dispersed in a consistent or even manner along any axis. Thus, while not exactly the same, the general composition of areas 430 and 440 are similar even at the microscopic level.

Due to the inclusion of conductive fillers, such as conductive nanoparticles 410 and/or conductive stabilizers 415, the composite polymeric foam 450 can exhibit negative piezoresistivity and a piezoelectric response to an impact or other deformation applied along any axis, such as the x axis, the y axis, and the z axis. Put another way, the measured electrical response is consistent in any direction over a same distance. For example, if an electrical response is detected along a first axis, a same distance is any distance within a sphere where the first axis is the diameter. Thus, when used as a sensor, composite polymeric foam 450 that is isotropic is not limited to measuring impacts that arrive from a predetermined orientation with respect to the composite polymeric foam 450. When composite polymeric foam 450 is anisotropic the composite polymeric foam 450 may measure impacts arriving from a predetermined orientation more accurately.

A material that exhibits a piezoresistive effect changes electrical resistance when compressed. A sensor with a negative piezoresistive effect becomes less resistant with increased strain, meaning a current will flow more easily through the material when compressed than through the material in its resting state. On the other hand, a gauge with a positive piezoresistive effect becomes more resistant with increased strain, meaning a current will not flow as easily. Traditional strain sensors measure strain by utilizing positive piezoresistivity; i.e., the electrical resistance increases with increased strain. The increased resistance in traditional strain gauges occurs due to Poisson-thinning of the strain gauge material. When a current producing device, such as a battery, is operatively coupled to the material, a change in the current may be measured as the material undergoes deformation. A sensor with a negative piezoresistive effect may be desirable for many applications since it will draw little or no current when the material is not strained, potentially prolonging the service time for battery powered applications. The change in electrical resistance is one type of electrical response to pressure/impact.

On the other hand, a material that produces a piezoelectric response generates electric potential, in the form of a voltage that can be measured when deformed. Thus, a material that produces a piezoelectric response may generate a voltage that can be measured without the need for an external current producing device. The voltage generated is another type of electrical response to impact. A material that exhibits a piezoresistive effect does not automatically produce a piezoelectric response and vice versa. However, composite polymeric foam 450 can exhibit both piezoresistive and piezoelectric responses. In some implementations, the shoe based analysis system may use piezoresistive voltage data to measure strain whereas the shoe-based analysis system may use piezoelectric voltage data to measure impact, i.e. both strain rate and total strain. In some implementations, the piezoresistive voltage data provides better feedback when the strain activity is slower, while the piezoelectric voltage data provides better feedback for faster impacts. The shoe-based analysis system may combine the piezoresistive and piezoelectric information for superior measurements.

Due to the inclusion of conductive stabilizers 415, the composite polymeric foam 450 can exhibit improved thermal conductivity. Put another way, by itself the matrix 405 may have low thermal conductivity, making the matrix 405 an insulator. However, the addition of a small percentage of conductive stabilizers 415, for example from 0.05% to 7.0% by weight, the thermal conductivity of the composite polymeric foam greatly increases without adversely affecting the mechanical material properties or feel of the matrix 405. Thus, for example, the composite polymer foam 450 can conduct heat away from the foot of the wearer. In one implementation the amount of conductive stabilizers 415 is approximately 0.05% to 7.0% of the weight of the polymer matrix 405. In some implementations, the load weight may be dependent on the length of the conductive fibers. At higher load weights the inclusion of the conductive stabilizers 415 may adversely affect the material properties of the resulting composite polymer foam 450.

The composite polymeric foam 450 is capable of being sculpted in any direction without affecting the piezoelectric response or the piezoresistive effect of the composite material because it is uniform between outer surfaces. In other words, because the composite polymeric foam 450 does not include layers, it may be cast and then cut or sculpted in any direction without affecting its ability to act as a piezoelectric or piezoresistive sensor. Thus, for example, a large sheet or block of the material may be manufactured and many sensors cut or formed from the same sheet. Moreover, the composite polymeric foam 450, once cured, does not need to be charged; the piezoelectric response is inherent in the composite polymeric foam 450 itself. Due to the elasticity of the matrix 405, the composite polymeric foam 450 is able to measure 80% strain without permanent deformation. This makes the composite polymeric foam 450 useful as a sensor in a shoe, which can experience strains on the order of 5% to 50%.

Implementations are not limited to a composite polymeric foam 450 that includes both conductive nanoparticles 410 and conductive stabilizers 415. FIG. 4B illustrates an implementation of composite polymeric foam 450 that includes the polymer matrix 405, voids 420, and the conductive nanoparticles 410 as the conductive filler without the conductive stabilizer. FIG. 41C illustrates another implementation of composite polymeric foam 450 that includes the polymer matrix 405, the voids 420, and the conductive stabilizers 415 as the conductive filler without the conductive nanoparticles. The variations of composite polymeric foam 450 illustrated in FIGS. 4A through 4C all exhibit a piezoelectric response and have negative piezoresistivity. The amounts and types of conductive fillers used affect the amount of energy absorption of the composite polymeric foam 450, the cost of the composite polymeric foam 450, the strength of the piezoresistive effect, the strength of the piezoelectric response, etc. It is recognized that the amounts and ratios may be dependent on many factors, such as the function of the composite material as padding or protection, the desired cost, the anticipated amplitude of impacts, etc. However, to exhibit the piezoelectric response the conductive fillers are generally 22% or less of the weight of the resulting composite polymeric foam 450. In some implementations, the conductive stabilizers may be generally up to 7% of the weight. In some implementations, the conductive nanoparticles 410 may generally be up to 15% of the weight.

Figure 5:
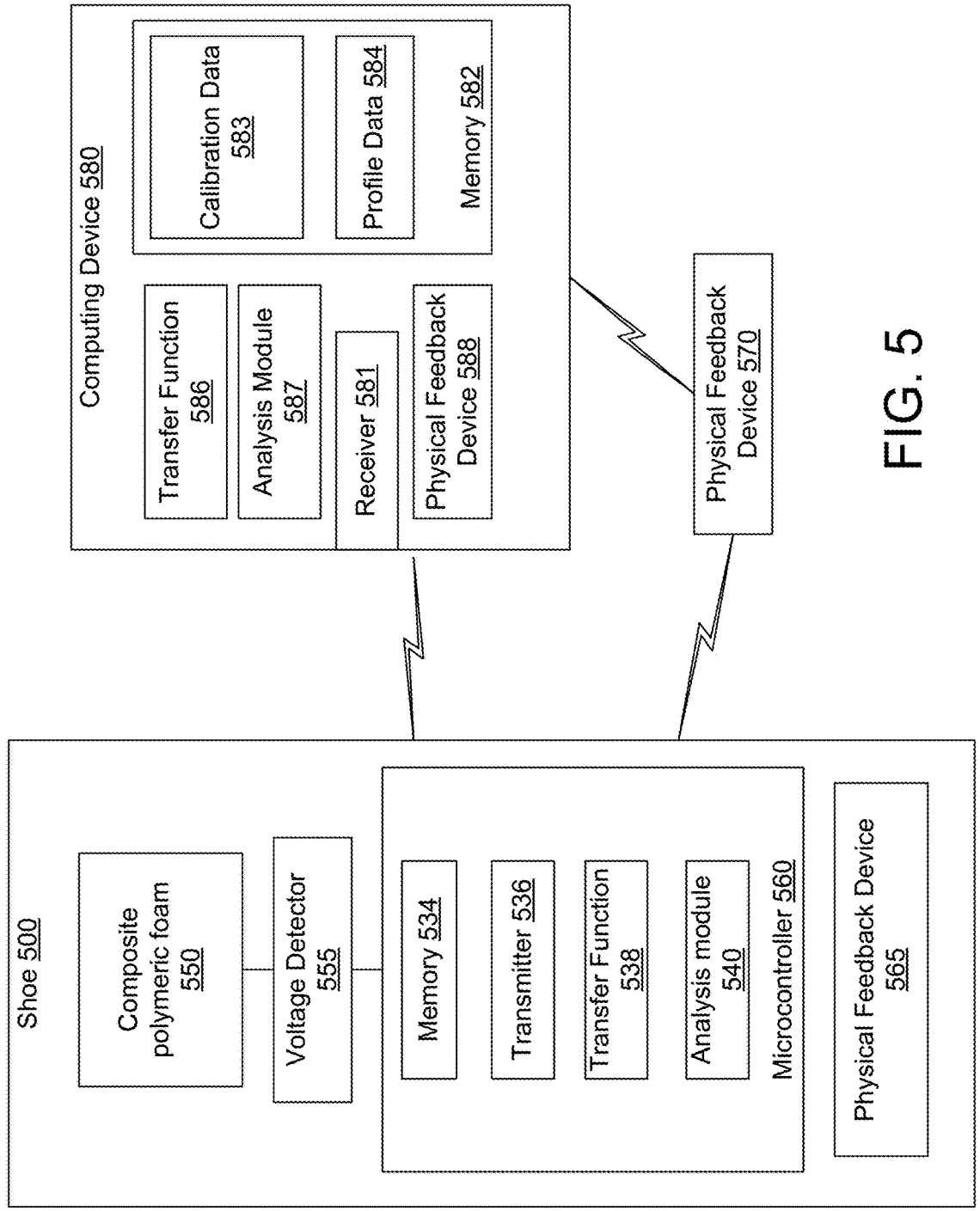
FIG. 5 is a block diagram that illustrates a shoe-based analysis system, according to an implementation.

FIG. 5 is a high-level block diagram that illustrates a shoe-based analysis system 590, according to an implementation. The system 590 includes a shoe 500 that includes self-sensing composite polymer foam 550. The composite polymer foam 550 replaces a portion of or all of the foam material in at least one part of the shoe 500. For example, the composite polymer foam 550 may replace one or more portions of the sock liner, the insole, the midsole, the outsole, the tongue, or any other padding in the shoe. The composite polymeric foam 550 may thus function as a padded insert as well as a sensor. The composite polymeric foam 550 may be composite polymeric foam 450 described with respect to FIGS. 4A through 4C. The composite polymeric foam 550 may be sensors 250(a) or 250(b) of FIG. 2A or sensor 350 of FIG. 3. Although illustrated as one sensor 550, implementations may include multiple sensors, e.g., multiple distinct areas of composite polymeric foam 550. Thus composite polymeric foam 550 represents one or more sensors in the shoe 500. The shoe 500 may include one or more voltage detectors 555 operatively coupled to the composite polymeric foam 550. In some implementations, the voltage detector 555 may be coupled to the composite polymeric foam 550 via one or more pairs of wires or other probes disposed in the composite polymeric foam 550. In some implementations the shoe 500 may include a plurality of voltage detectors 555, operatively coupled to respective sensors (e.g., sensor 250(a) and sensor 250(b) of FIG. 2A may each have a respective voltage detector 555) or to a single sensor (e.g., sensor 350 of FIG. 3 may be coupled to multiple voltage detectors 555). The voltage detector 555 may be capable of detecting voltage generated by the composite polymeric foam 550 when the composite polymeric foam 550 experiences strain, for example due to an impact. The voltage detector 555 may also be capable of detecting a decrease in electrical resistance when the composite polymeric foam 550 experiences strain, for example due to an impact. In such an implementation, the shoe 500 may include a voltage source (e.g., a battery, not shown). The voltage detector 555 may be any device that detects or uses voltage and produces a value that can be stored and/or compared. In some implementations, the voltage detector 555 may also include other components (not shown), such as memory and/or a processor, (e.g., a processor formed in a substrate).

The voltage detector 555 may be operatively coupled to or included in a microcontroller 560. The microcontroller 560 may include a memory 534 and/or a transmitter 536. The memory 534 may be any type of volatile or non-volatile memory capable of storing voltage data. In some implementations, the voltage detector 555 may be capable of converting detected voltage into a value that is stored in the memory 534. In some implementations (not shown), the memory 534 may be a component of the voltage detector 555. In some implementations, the memory 534 may store additional information with the voltage value, such as the date and/or time the value was detected. In some implementations, with multiple voltage detectors 555, the additional information may include an identifier of the voltage detector that detected the value. The memory 534 may also store other information with the voltage value. The voltage value and additional information, if any, are considered voltage data. Thus, the memory 534 may store voltage data detected after a strain event, such as an impact received by the composite polymeric foam 550. In some implementations, the memory 534 may store a plurality of voltage data, representing a plurality of strain events. The memory 534 may store the plurality of voltage data until it is transmitted to a computing device, either wirelessly or via a wired connection.

In some implementations, the memory 534 may also store profile data. The profile data may represent a series of values representing compression events having a target or ideal sequence. For example, the profile data may represent ground reaction force data for an ideal sprinting stride, during an ideal hurdle stride, during an ideal walking stride, during an ideal golf swing, etc. The ground reaction force data may represent the force at different points on the foot, e.g., at the heel, at the toe, at the ball, at the inner arch, and/or the outer arch, etc.

In some implementations, the microcontroller may include transfer function 538. Transfer function 538 represents instructions that, when executed by the microcontroller 560, converts the voltage data from the voltage detector 555 to force data, such as ground reaction force, pressure, acceleration, etc. Each different type of force may have a corresponding transfer function 538. Thus, the transfer function for ground reaction force differs from the transfer function for pressure. The microcontroller may also include an analysis module 540 configured to compare the force data, or in other words the converted voltage data generated by the composite polymeric foam 550, to a profile. When significant differences are found between the profile and the force data, e.g., values fail to fall within a threshold value of the profile values, the analysis module 540 may be configured to initiate feedback via a physical feedback device that alerts the wearer of the shoe 500. The physical feedback device can be included in the shoe 500, such as physical feedback device 565 or can be on a remote computing device, such as physical feedback device 570 or 588.

For example, the physical feedback device 565 in the shoe 500 may be a device that vibrates, produces sound, displays a pattern of light, etc. The pattern of light can be a light of a specific color, two lights displaying a combination of colors, a solid color light that flashes in a pattern, etc. In some implementations, the vibration sequence, the sounds, or the light pattern indicates to the wearer either that the wearer's movements differ from the profile. In some implementations, the vibration sequence, sounds, or light pattern may indicate a specific problem with the wearer's movements. For example, a blue light may indicate incorrect heel strike, a yellow light too much pronation, an orange light not enough acceleration, etc. Similar vibration sequences, e.g., two quick pulses for improper heel strike, one long vibration for improper pronation, or sounds can be used to differentiate different problems. The microcontroller 560 may have a wired or wireless connection with the physical feedback device.

In some implementations, the memory 534, transfer function 538, and/or analysis module 540 may be operatively coupled to a transmitter 536. The transmitter 536 may be capable of transmitting data wirelessly to a computing device 580 or a physical feedback device, such as device 565 or device 570. The microcontroller 560 may thus be a wireless microcontroller, for example the RFdigital RFduino. In some implementations, the transmitter 536 may transmit the voltage data or a feedback signal, e.g., which type of feedback to provide, in response to data being stored in the memory 534. In some implementations, the voltage data or feedback signal may be wirelessly transmitted in real-time. In some implementations, the transmitter 536 may transmit the feedback signal in response to identifying differences between a profile and voltage data or force data. In some implementations, the microcontroller 560 may not include transfer function 538 and/or analysis module 540. In some implementations, the shoe 500 may not include physical feedback device 565. In such an implementation, the transmitter 536 may transmit the voltage data as soon as the transmitter 536 receives voltage data or force data.

The transmitter 536 may transmit voltage data, force data, and/or a feedback signal to a computing device 580. The computing device 580 may be an external computing device, separate from the shoe 500. In such implementations, the computing device 580 may include a receiver 581. The computing device 580 may be any type of computing device, such as a controller (e.g., a processor, a microcontroller, etc.), a tablet, a laptop, a smart phone, a server, personal computer, a television with a processor, a smart watch or other wearable computing devices such as a fitness tracker or glasses, etc. The computing device 580 may include one or more transfer functions 586. The transfer functions 586 may be configured to translate the voltage data generated by the composite polymeric foam 550 into one of several types of mechanical data, e.g., ground reaction force, pressure, acceleration, leg stiffness, etc. In some implementations, the transfer function 586 may have access to calibration data 583 that enables the transfer function 586 to convert the voltage data into the aforementioned mechanical data. In some implementations, the transfer function 586 may have access to calibration data 583 that enables the transfer function 586 to convert the voltage data into energy expenditure data. The transfer function may depend upon single or multiple voltage or electrical resistance inputs which are combined through the use of statistical methods such as basis expansions (e.g., functional data analysis) and regression or similar statistical tools to provide a calibrated force, strain, or displacement reading. For example, the individual vector components of the ground reaction force may be computed based on algebraic combination of voltage inputs from several self-sensing polymeric foam inserts located in various locations on the shoe. In some implementations, the transfer function 586 may be or may include a machine learning algorithm that has been trained on patterns identified in the voltage data. For example, the transfer function may also be adapted "real-time" based on a machine learning algorithm that identifies and removes noise and drift from the input signals. As another example, the transfer function may include a machine learning algorithm that finds patterns in the voltage data provided and identifies key points that correlate to mechanical data (e.g., acceleration, energy expenditure, leg stiffness, pressure, ground reaction force, etc.). In some implementations, the transfer functions 586 can be excluded, for example when transfer functions 538 exist. In some implementations, the transfer functions 586 may coordinate with transfer functions 538. In some implementations, the shoe 500 may include transfer function 538 that has the capabilities of transfer function 586 when memory 534 stores the calibration data 583.

The computing device 580 may also include a calibration data 583. The calibration data 583 may be used by the transfer function 586 (or 538) to analyze and interpret the voltage data. In some implementations the calibration data 583 may be provided to the computing device 580. In some implementations, the computing device 580 may include a module (not shown) that collects and stores the calibration data 583. The calibration data 583 may represent force data, strain/displacement data, or energy expenditure data. Because the composition of the composite polymeric foam 550, for example the amount of conductive nanoparticles and the amount of conductive stabilizers, can affect the piezoresistive and piezoelectric properties of the composite polymeric foam 550, composite polymeric foam 550 that is manufactured outside of a controlled environment (e.g., outside of an established manufacturing process) may need to be calibrated after each manufacture. Composite polymeric foam 550 that is manufactured in a controlled environment, however, nay not need calibration after every manufacture.

The computing device 580 may also include analysis module 587. The analysis module 587 may use force data from one or more transfer functions 586 and compare the force data (i.e., generated from the voltage data produced by the composite polymeric foam 550) to an activity profile in profile data 584. The profile data 584 may represent a series of values representing compression events having a target or ideal sequence. For example, a profile in the profile data 584 may represent ground reaction force data, pressure data, and/or acceleration data for an ideal sprinting stride, another profile in the profile data may represent ground reaction force data, pressure data, and/or acceleration data for an ideal hurdle stride, another profile may represent an ideal walking stride, another profile may represent an ideal golf swing, etc. The force data in a profile may represent the force at different points on the foot during the motion, e.g., at the heel, at the toe, at the ball, at the arch, and/or opposite the arch, etc., during a series of steps or pedaling. The analysis module 587 may be configured to compare force data from the shoe 500 with one or more profiles in real time, e.g., as the wearer of the shoe 500 is sprinting, is pedaling, or is walking. When the analysis module 587 identifies a difference between the force data from the shoe 500 and the profile, the analysis module 587 may provide a feedback signal to a physical feedback device. The feedback signal may be a particular vibration pattern, a sound, a light pattern, or an image (including text) to display.

The physical feedback device can be part of the shoe 500, part of computing device 580, or another physical feedback device 570. Thus, physical feedback device 565 may be excluded when physical feedback device 588 receives the feedback signal. Likewise, physical feedback device 588 may be excluded when physical feedback device 565 receives the feedback signal. Similarly, physical feedback device 588 and physical feedback device 565 may be eliminated when physical feedback device 570 receives the feedback signal. In some implementations, the physical feedback device 565, the physical feedback device 588, and/or the physical feedback device 570 may coordinate, e.g., they may each receive a feedback signal and provide feedback to the wearer. In some such implementations each device may provide a different type of feedback.

Similarly, in some implementations, one or more of the functions of the analysis module 587 is included in the shoe 500, e.g., as analysis module 540. Thus, module 540 and module 587 may coordinate. In some implementations, the analysis module 587 may be excluded and analysis module 540 may perform the functions described above. In some implementations, the analysis module 540 may be eliminated.

In some implementations, the shoe 500 may provide feedback for orthopedic fittings, training and caloric output, etc. using computing device 580. In such implementations, the shoe 500 may store a plurality of voltage data, corresponding to respective impact events, that is transmitted to computing device 580 at the request of a user, an external computer, etc. In some implementations, the shoe 500 may provide real-time biometric feedback to help a wearer correct stride, gait, or other form. In some implementations, the shoe 500 may include all hardware and software, e.g., transfer function 538, profile data 584, physical feedback device 565, to provide the feedback. In some implementations the shoe 500 may communicate with the computing device 580 to determine the feedback. In some implementations, the shoe 500 may determine the feedback and may initiate the feedback, e.g., via communication with an external physical feedback device 570 that provides the physical feedback. The physical feedback device 570 may be a wearable item that has the ability to vibrate, play sounds, or display lights or information to the wearer. In such implementations a computing device 580 that is separate from shoe 500 is not needed.

Figure 6:
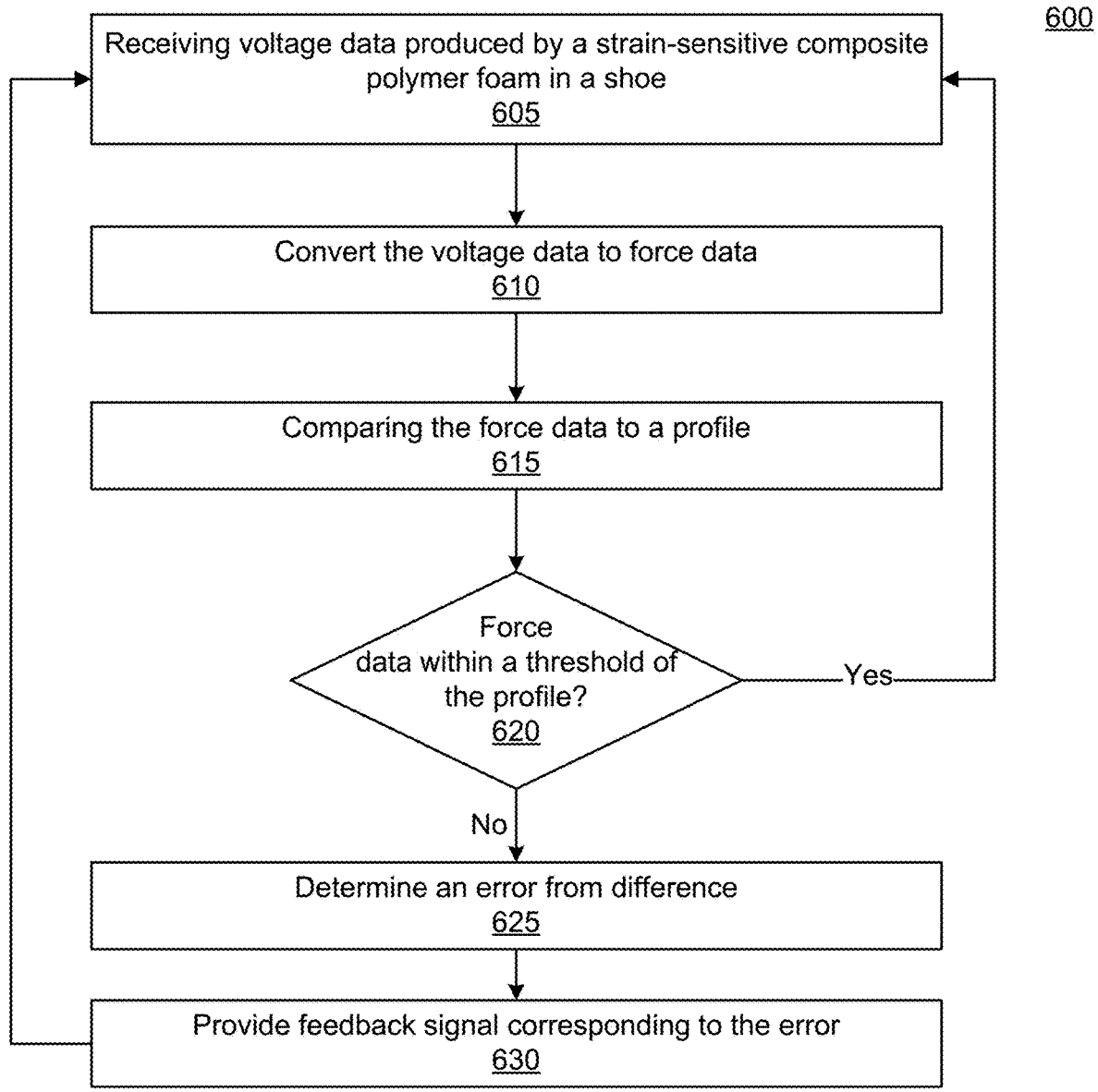
FIG. 6 is a flow diagram of a process for providing physical feedback using the shoe-based analysis system, according to an implementation.

FIG. 6 is a flow diagram of an example process 600 for providing physical feedback using the shoe-based analysis system, according to an implementation. Process 600 may be used in a shoe-based analysis system, such as system 590 of FIG. 5, to provide real-time feedback to the wearer of the shoe during physical activity, such as sprinting, kicking, walking, golfing, etc. Process 600 enables the wearer of the shoe to correct form while the wearer performs the activity. For example the feedback enables the wearer to determine incorrect stride, gait, weight shifting (e.g., during a golf swing), etc. Process 600 is understood to execute continuously once started until interrupted. In this manner, process 600 can provide continuous feedback during a particular physical activity session. In some implementations, once the session ends the voltage data produced during the activity session may be stored or transmitted, wirelessly or via a wired connection, to a computing device for storage and further analysis.

Process 600 begins with the system receiving voltage data produced by a strain-sensitive composite polymer foam in a shoe (605). The strain-sensitive composite polymer foam may replace at least a portion of existing foam in the shoe or may be an insert (e.g., insole insert or a heel insert). The strain-sensitive composite polymer foam may function as padding in the shoe. The strain-sensitive composite polymer foam may be composite polymer foam 450 of FIG. 4. The composite polymer foam is able to produce or generate both piezoresistive and piezoelectric responses to deformation events. Voltage data may be produced at each site where a probe is disposed in the composite polymer foam. The shoe may have multiple portions of existing foam replaced with the composite polymer foam, or the composite polymer foam may have multiple probes disposed therein. In some implementations, the probes may correspond to a particular part of the wearer's foot. For example, the probes may correspond to the toes, the ball, the heel, the top, the sides, etc. depending on the placement of the composite polymeric foam in the shoe and the placement of the probes in the composite polymeric foam.

The system may convert the voltage data to force data (610). The system may have at least one transfer function for converting the voltage data to a particular kind of force. For example, one transfer function may convert the voltage data to ground reaction force data. Another transfer function may convert the voltage data to pressure data. Because the composite polymeric foam can produce both piezoelectric and piezoresistive data concurrently from a single deformation event, the system may calculate both pressure data and ground reaction force data from the same voltage data. The transfer functions are discussed in more detail with regard to FIGS. 7 to 9.

The system may compare the force data to an activity profile (615). The profile may represent ideal force data for a particular activity. The profile may include data corresponding to particular portions of the foot, e.g., values that correspond to the toes, the ball, the heel, etc. In other words, the profile data may have values that correspond to the different probe locations. The system may determine whether the force data obtained using the composite polymer foam falls within a threshold of the profile (620). In other words, the system may compare the force data for each foot location to corresponding profile data. If all values are within the threshold (620, Yes), the system may continue receiving voltage data (605).

If any values fall outside the threshold (620, No), the system may consider the values to be errors and determine the error(s) (625). In some implementations, an error may represent any value that falls outside the threshold. In some implementations, an error may correspond to a particular part of the foot, or in other words to a particular probe location. The system may provide a feedback signal corresponding to the error (630). In some implementations, any error may correspond with the same feedback signal. In some implementations, e.g., where the error corresponds to a particular probe location, the system may be configured to provide a different feedback signal for each specific error. In other words, the system may be able to provide feedback that indicates to the wearer exactly how the physical activity fails to conform to the profile. For example, if the profile is for sprinting, the feedback signal may indicate that the force has been applied to a location of the foot that may increase injury risk or decrease performance. Other measures that may be of interest and measured by the shoe include: stride rate, stride length, braking or impulsive propulsion, leg stiffness and changes in momentum. Such measures may be used, for example, to objectively measure gait-related tasks that must be passed before a patient is discharged from the hospital. As another example, if the profile is for a golf swing, the feedback signal may indicate that weight was too far forward on the back foot. As a therapeutic example, the feedback signal might indicate that an osteoarthritic patient is moving in a way that unnecessarily increases ground reaction force or pressure, and increases the rate of disease progression. In some implementations, the physical feedback device may continue to provide the feedback (e.g., continue to play the sound or display the light pattern) until the force data is within the threshold for the profile data.

Figure 7:
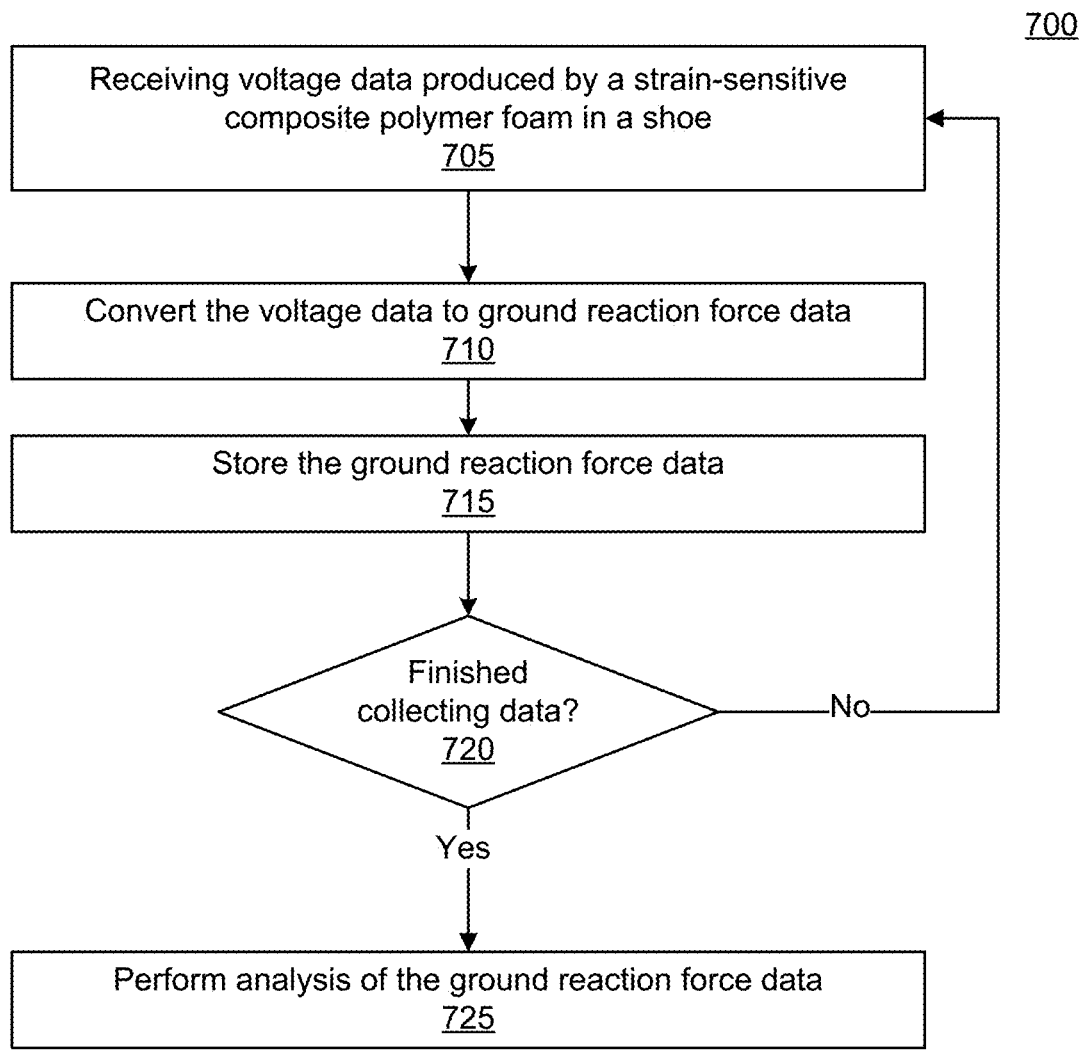
FIG. 7 is a flow diagram of a process for generating ground reaction force data using the shoe-based analysis system, according to an implementation.

FIG. 7 is a flow diagram of an example process 700 for generating ground reaction force data using the shoe-based analysis system, according to an implementation. Process 700 may be executed by a shoe-based analysis system, such as system 590 of FIG. 5. Process 700 generates ground reaction force data that correlates to the ground reaction force data conventionally obtained in very expensive laboratory settings. However, process 700 takes place outside of any laboratory using a shoe with at least some of its foam padding (e.g., in the sole, tongue, sides, etc.) replaced with strain-sensitive composite polymer foam. The ground reaction force data obtained in a laboratory setting has been used to diagnose fatigue, depression, injury, concussion, Parkinson's, Alzheimer's, etc. Because the ground reaction force data generated by the shoe-based analysis system, e.g., system 590, correlates to the data generated in a laboratory, these same types of diagnoses can result from process 700.

Process 700 may begin with the system receiving voltage data produced by a strain-sensitive composite polymer foam in a shoe (705). The strain-sensitive composite polymer foam may replace at least a portion of existing foam in the shoe or may be an insert (e.g., insole insert or a heel insert). The strain-sensitive composite polymer foam may function as padding in the shoe. The strain-sensitive composite polymer foam may be composite polymer foam 450 of FIG. 4. The composite polymer foam is able to produce or generate both piezoresistive and piezoelectric responses to deformation events. Voltage data may be produced at each site where a probe is disposed in the composite polymer foam. The shoe may have multiple portions of existing foam replaced with the composite polymer foam, or the composite polymer foam may have multiple probes disposed therein. In some implementations, the probes may correspond to a particular part of the wearer's foot. For example, the probes may correspond to the toes, the ball, the heel, the top, the sides, etc. depending on the placement of the composite polymeric foam in the shoe and the placement of the probes in the composite polymeric foam.

The system may convert the voltage data to ground reaction force data (710). Converting the voltage data to ground reaction force data, or other data such as acceleration data or pressure data, may occur through the use of statistical methods such as basis expansions (e.g., functional data analysis) and regression or similar statistical tools.

In one example, to convert shoe sensor data to ground reaction force (GRF) (or acceleration data or pressure data), the system begins with shoe sensor data, i.e., the voltage data produced by the composite polymeric foam, and GRF data for a collection of training stances. The GRF data for a collection of training stances is training data obtained in a laboratory setting. The system may filter the shoe sensor data with a Butterworth filter and then apply functional data analysis tools to create functional representations of the shoe sensor curves and GRF curves. The system may use any basis expansion (wavelets, B-splines, other Fourier-based methods, etc.) to represent the shoe sensor curves. The system may obtain coefficients associated with these representations and use variable selection methods (e.g., backward elimination) to select the coefficients that are retained. For example, to predict a particular stance, the system may obtain a prediction of the p parameters associated with a GRF curve $(\theta_1, \ldots, \theta_p)$ from the q estimated parameters associated with the shoe sensor curves $(\varphi_1, \ldots, \varphi_q)$ using $$\theta = B \varphi$$

where $\theta=(\theta_1, \ldots, \theta_p)'$, $\varphi=(1, \varphi_1, \ldots, \varphi_q)'$, and B is a p×(q+1) matrix of coefficients obtained from the regression of $\theta$ on $\varphi$ from the training data. Once the estimated parameter vector $\theta$ is obtained for the particular stance, the associated predicted GRF (or acceleration or pressure) curve can be obtained by reconstructing a curve from $\theta$.

In some implementations, the conversion takes place on a microcontroller in the shoe. In some implementations, the shoe may include a microcontroller that transmits the voltage data to another computing device where the conversion takes place. The system may store the ground reaction force data in a memory (715). In some implementations, the shoe may include memory in which the ground reaction force data is stored. In some implementations, the shoe may transmit the ground reaction force data to another computing device for storage. The ground reaction force data may represent data corresponding to particular parts of the foot, or a resultant ground reaction force vector that is applied to the foot at the center of pressure. The ground reaction force data may include components related to the toes, ball, heel, inner arch, outer arch, etc., depending on the location of the composite polymer foam and the placement of probes in the composite polymer foam.

The system may determine whether it is finished collecting data (720). For example, the system may collect data for a specific time period or until it receives an explicit command to stop. In some implementations, the explicit command may be a command to transfer the saved data. If it is not finished (720, No), the system continues receiving voltage data (705). If the system is finished (720, Yes), the system may perform analysis of the ground reaction force data (725). The analysis can include analysis that results in the diagnoses addressed above, as well as additional analysis, such as determining the weight of the wearer, deterring caloric burn during a session, the height of a jump, cadence, stride length, propulsion, braking, etc.

Figure 8:
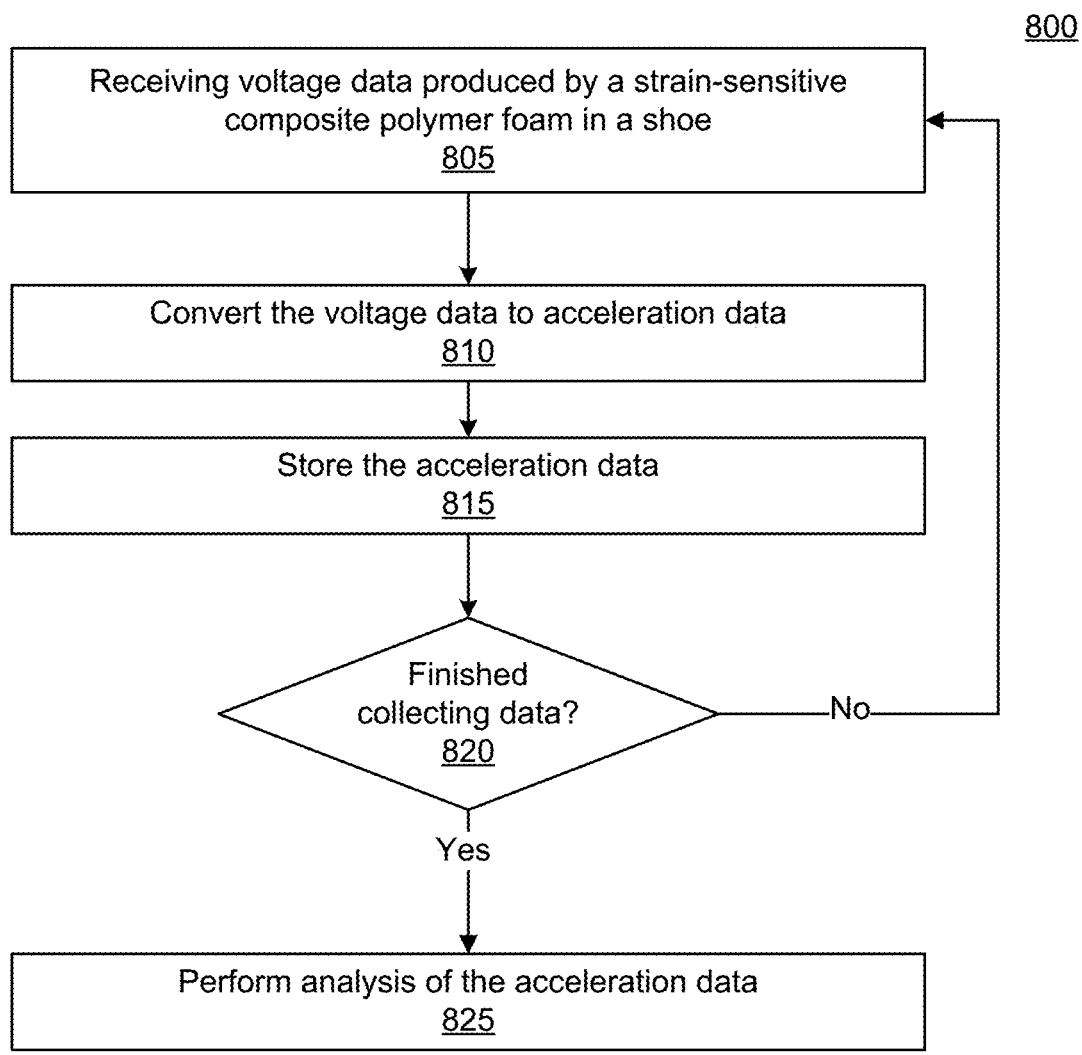
FIG. 8 is a flow diagram of a process for generating acceleration data using the shoe-based analysis system, according to an implementation.

FIG. 8 is a flow diagram of an example process 800 for generating acceleration data using the shoe-based analysis system, according to an implementation. Process 800 may be executed by a shoe-based analysis system, such as system 590 of FIG. 5. Process 800 generates acceleration data that correlates to acceleration data conventionally obtained in very expensive laboratory settings. However, process 800 takes place outside of any laboratory using a shoe with at least some of its foam padding (e.g., in the sole, tongue, sides, etc.) replaced with strain-sensitive composite polymer foam. Among other things, the acceleration data obtained in a laboratory setting has been used to learn more about forces and motion, during human motion, that relate to increased human performance or injury risk. Because the acceleration data generated by the shoe-based analysis system, e.g., system 590, correlates to the data generated in a laboratory, these same types of uses can result from process 800. Process 800 may be run concurrently with process 700 because the voltage data can be provided to two different transfer functions simultaneously.

Process 800 may begin with the system receiving voltage data produced by a strain-sensitive composite polymer foam in a shoe (805). The strain-sensitive composite polymer foam may be composite polymer foam 450 of FIG. 4. Voltage data may be produced at each site where a probe is disposed in the composite polymer foam. The shoe may have multiple portions of existing foam replaced with the composite polymer foam, or the composite polymer foam may have multiple probes disposed therein. In some implementations, the probes may correspond to a particular part of the wearer's foot. For example, the probes may correspond to the toes, the ball, the heel, the top, the sides, etc. depending on the placement of the composite polymeric foam in the shoe and the placement of the probes in the composite polymeric foam.

The system may convert the voltage data to acceleration data (810). In some implementations, the system may use a transfer function that has been trained using a machine learning algorithm to find key data points in the voltage data generated by the composite polymer foam. In some implementations, converting the voltage data to acceleration data may occur through the use of statistical methods such as basis expansions (e.g., functional data analysis) and regression or similar statistical tools. In some implementations, the conversion takes place on a microcontroller in the shoe. In some implementations, the shoe may include a microcontroller that transmits the voltage data to another computing device where the conversion takes place. The system may store the acceleration data in a memory (815). In some implementations, the shoe may include memory in which the acceleration data is stored. In some implementations, the shoe may transmit the acceleration data to another computing device for storage. The acceleration data may represent data corresponding to particular parts of the foot. For example, the acceleration data may include components related to the toes, ball, heel, inner arch, outer arch, etc., depending on the location of the composite polymer foam and the placement of probes in the composite polymer foam.

Figure 9:
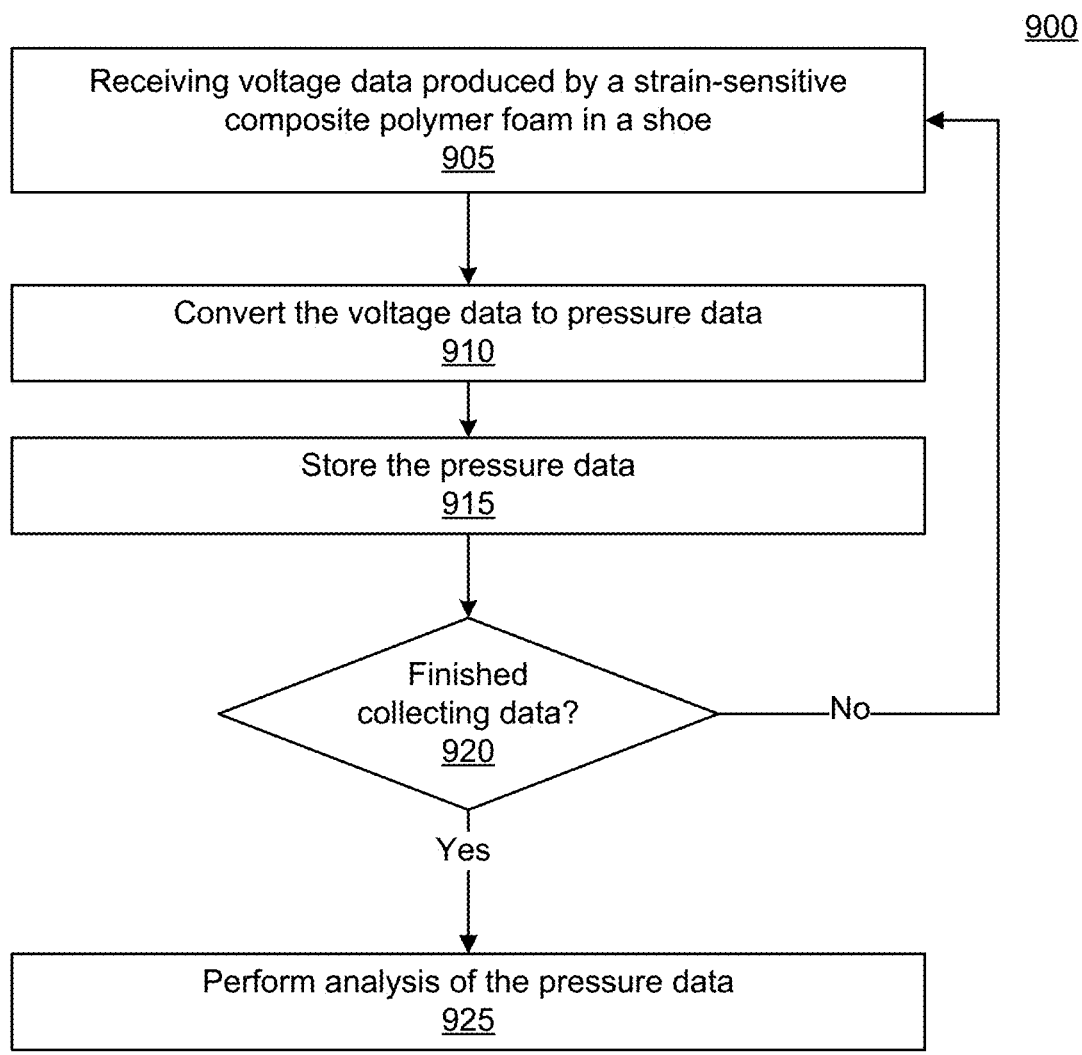
FIG. 9 is a flow diagram of a process for generating pressure data using the shoe-based analysis system, according to an implementation.

The system may determine whether it is finished collecting data (820). For example, the system may collect data for a specific time period or until it receives an explicit command to stop. In some implementations, the explicit command may be a command to transfer the saved data. If it is not finished (820, No), the system continues receiving voltage data (805). If the system is finished (820, Yes), the system may perform analysis of acceleration data (825). The analysis can include, braking and propulsion measurements, FIG. 9 is a flow diagram of a process for generating pressure data using the shoe-based analysis system, according to an implementation. Process 900 may be executed by a shoe-based analysis system, such as system 590 of FIG. 5. Process 900 generates pressure data that correlates to pressure data conventionally obtained by more expensive instruments that are often found in laboratory settings. However, process 900 takes place outside of any laboratory using a shoe with at least some of its foam padding (e.g., in the sole, tongue, sides, etc.) replaced with strain-sensitive composite polymer foam. The pressure data obtained in a laboratory setting has been used to evaluate human performance during various physical activity (e.g., running patterns), and diagnosis and treatment of various common pathologies (e.g., diabetic neuropathy). Because the pressure data generated by the shoe-based analysis system, e.g., system 590, correlates to the data generated in a laboratory, these same types of uses can result from process 900. Process 900 may be run concurrently with process 700 and/or 800 because the same voltage data can be provided to multiple transfer functions.

Process 900 may begin with the system receiving voltage data produced by a strain-sensitive composite polymer foam in a shoe (905). The strain-sensitive composite polymer foam may replace at least a portion of existing foam in the shoe or may be an insert (e.g., insole insert or a heel insert). The strain-sensitive composite polymer foam may function as padding in the shoe. The strain-sensitive composite polymer foam may be composite polymer foam 450 of FIG. 4. As one example, replacement of the foam in the tongue of the shoe may enable the system to measure the force of a kick. Another example involves the measurement of and then subsequent decrease of high pressure that is applied to the heel of the foot of a patient who suffers from decubitus ulcers that are commonly secondary to other pathologies. Voltage data may be produced at each site where a probe is disposed in the composite polymer foam. The shoe may have multiple portions of existing foam replaced with the composite polymer foam, or the composite polymer foam may have multiple probes disposed therein. In some implementations, the probes may correspond to a particular part of the wearer's foot. For example, the probes may correspond to the toes, the ball, the heel, the top, the sides, etc. depending on the placement of the composite polymeric foam in the shoe and the placement of the probes in the composite polymeric foam.

The system may convert the voltage data to pressure data (910). In some implementations, the system may use a transfer function that has been trained using a machine learning algorithm to find key data points in the voltage data generated by the composite polymer foam. In some implementations, converting the voltage data to pressure data may occur through the use of statistical methods such as basis expansions (e.g., functional data analysis) and regression or similar statistical tools. In some implementations, the conversion takes place on a microcontroller in the shoe. In some implementations, the shoe may include a microcontroller that transmits the voltage data to another computing device where the conversion takes place. The system may store the pressure data in a memory (915). In some implementations, the shoe may include memory in which the pressure data is stored. In some implementations, the shoe may transmit the pressure data to another computing device for storage. The pressure data may represent data corresponding to particular parts of the foot. For example, the pressure data may include components related to the toes, ball, heel, inner arch, outer arch, etc., depending on the location of the composite polymer foam and the placement of probes in the composite polymer foam.

The system may determine whether it is finished collecting data (920). For example, the system may collect data for a specific time period or until it receives an explicit command to stop. In some implementations, the explicit command may be a command to transfer the saved data. If it is not finished (920, No), the system continues receiving voltage data (905). If the system is finished (920, Yes), the system may perform analysis of pressure data (925). The analysis can result in a quantification of pressure distribution across the entire plantar surface of the foot, which could be used to better understand various important characteristics of human performance and injury. The analysis would be helpful in various areas; e.g., a better understanding of movement efficacy in sport, more effective evaluations of acute concussion severity, or more understanding regarding the efficacy of a rehabilitative intervention designed to treat chronic ankle instability.

Analysis of a patient's walking and running mechanics can be a valuable tool in the Assessment and Rehabilitation of current injuries as well as the prevention of future injuries. Gait Analysis may be provided during a patient's initial evaluation, and revisited during later sessions to monitor progress. Any of methods 700, 800, or 900, alone or in combination, can be used as input for gait analysis. For example, the voltage data may be provided to a ground reaction force transfer function and to a pressure transfer function. The resulting ground reaction force data and pressure data may be compared against respective profiles concurrently. Thus, the shoe-based analysis system may provide feedback, e.g., in the form of a feedback signal to a physical feedback device, for ground reaction force and pressure profiles at the same time as part of gait analysis. The shoe-based analysis system could provide similar combined feedback for other types of mechanical data (e.g., ground reaction force and acceleration). Because the composite polymer foam sensors provide data for slower (e.g., piezoresistive) and faster (e.g., piezoelectric) strain events, and because the sensors are non-additive and essentially undetectable by the wearer, shoe-based analysis system provides a superior environment for collecting gait analysis data.

Figure 10A:
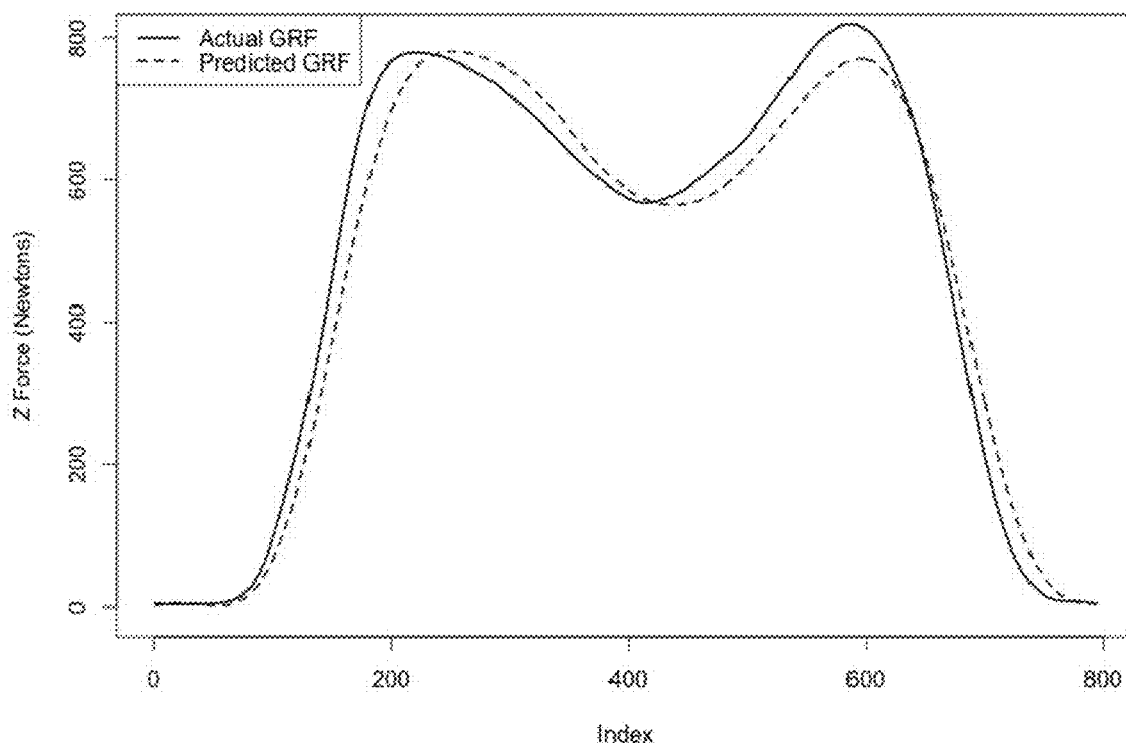
FIG. 10A to 10C are charts illustrating correspondence of ground reaction force data from an exemplary shoe-based analysis system with laboratory ground reaction force data, according to an implementation.
Figure 10B:
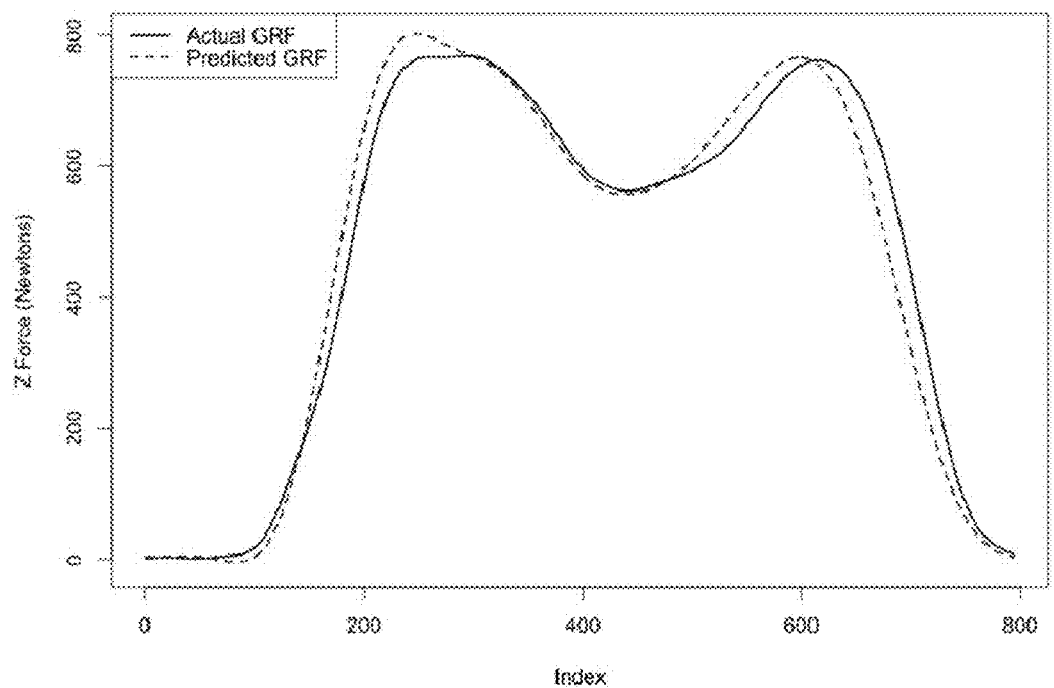
Figure 10C:
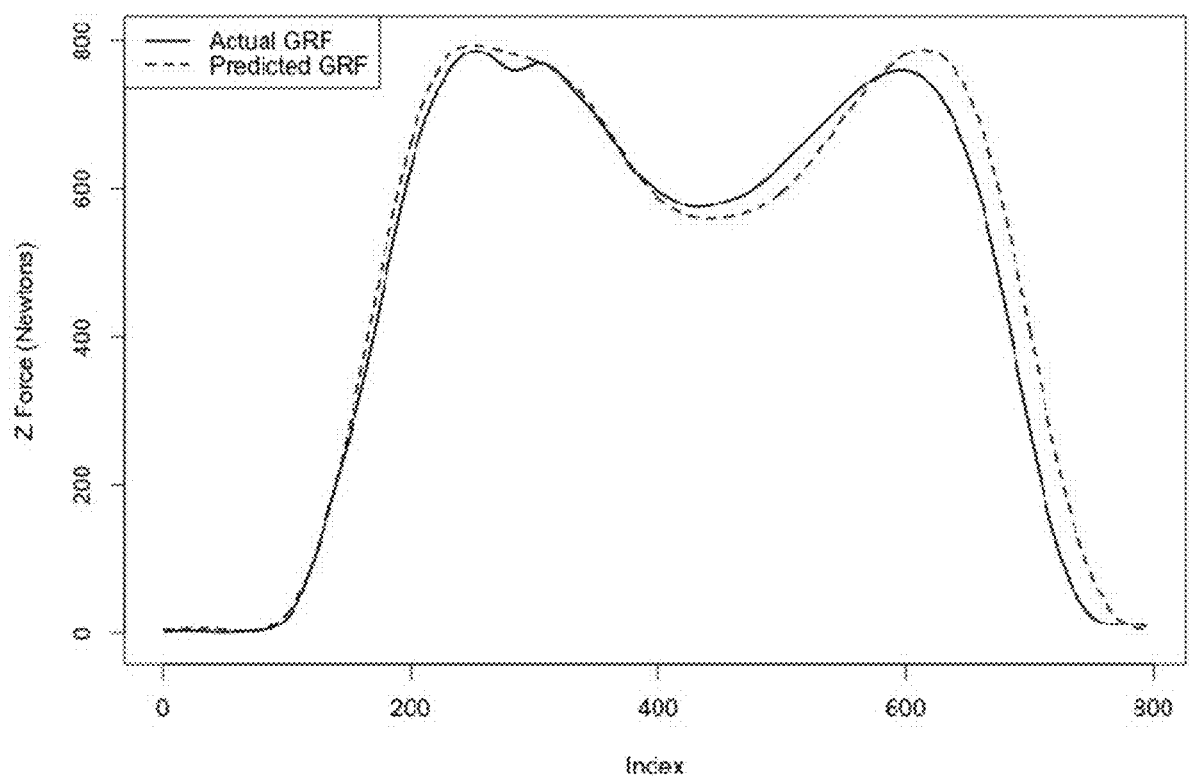

FIGS. 10A to 10C are charts illustrating correspondence of ground reaction force data from an exemplary shoe-based analysis system with laboratory ground reaction force data, according to an implementation. The charts compare a ground reaction force data collected from a lab-based system with predicted ground reaction force data obtained from a shoe-based analysis system, e.g., the system 590 of FIG. 5, that uses composite polymeric foam sensors. The actual lab-based ground reaction force data, i.e., the solid line in FIGS. 10A, 10B, and 10C, represents data obtained in an expensive laboratory setting, or in other words training data. The predicted GRF represents data obtained using the composite polymeric foam and a transform function. Each of FIGS. 10A, 10B, and 10C also illustrates the shoe-based prediction of the ground reaction force curve with a blue dashed line, with the prediction carried out using the approach outlined in paragraph 0054 above. The three figures are representations of three typical steps (stances) for ground reaction force in the vertical direction. FIG. 10A illustrates a ground reaction force of a first typical step. FIG. 10B illustrates ground reaction force of a second typical step. FIG. 10C illustrates ground reaction force of a third typical step. In some implementations, the steps of FIGS. 10A to 10C may also represent three steps in an example profile of profile data, e.g., stored in profile data 584 of FIG. 5. The profile that includes the three steps would likely include additional ground reaction force steps as well as pressure data for the steps and/or acceleration data for the steps. These graphs illustrate that the shoe-based analysis system can replicate ground reaction force data attached to any step. As indicated earlier, correlation with ground reaction force data obtained in laboratory settings means that shoe-based analysis system can provide high-quality ground reaction force data obtained in every-day settings that can be used to diagnose and correct many problems.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments. It should be understood that they have been presented by way of example only, not limitation, and various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described.

Implementations of the various techniques described herein may be implemented in digital electronic circuitry, or in computer hardware, firmware, software, or in combinations of them. Implementations may implemented as a computer program product, i.e., a computer program tangibly embodied in an information carrier, e.g., in a machine-readable storage device (computer-readable medium) or in a propagated signal, for processing by, or to control the operation of, data processing apparatus, e.g., a programmable processor, a computer, or multiple computers. A computer program, such as the computer program(s) described above, can be written in any form of programming language, including compiled or interpreted languages, and can be deployed in any form, including as a stand-alone program or as a module, component, subroutine, or other unit suitable for use in a computing environment. A computer program can be deployed to be processed on one computer or on multiple computers at one site or distributed across multiple sites and interconnected by a communication network.

Many of the method steps may be performed by one or more programmable processors executing a computer program to perform functions by operating on input data and generating output. Method steps also may be performed by, and an apparatus may be implemented as, special purpose logic circuitry, e.g., an FPGA (field programmable gate array) or an ASIC (application-specific integrated circuit).

Processors suitable for the processing of a computer program include, by way of example, both general and special purpose microprocessors, and any one or more processors formed in a substrate of any kind of digital computer. Generally, a processor will receive instructions and data from a read-only memory or a random access memory or both. Elements of a computer may include at least one processor for executing instructions and one or more memory devices for storing instructions and data. Generally, a computer also may include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory may be supplemented by, or incorporated in special purpose logic circuitry.

To provide for interaction with a user, implementations may be implemented on a computer having a display device, e.g., a liquid crystal display (LCD) monitor, or a touch screen for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Implementations may be implemented in a computing system that includes a back-end component, e.g., as a data server, or that includes a middleware component, e.g., an application server, or that includes a front-end component, e.g., a client computer having a graphical user interface or a Web browser through which a user can interact with an implementation, or any combination of such back-end, middleware, or front-end components. Components may be interconnected by any form or medium of digital data communication, e.g., a communication network. Examples of communication networks include a local area network (LAN) and a wide area network (WAN), e.g., the Internet.

In one general aspect, an apparatus includes a shoe having a sole, the sole having at least a portion of foam replaced with a self-sensing composite polymeric foam, at least one probe disposed in the self-sensing composite polymeric foam, a voltage detector coupled to the probe that detects voltage data generated by the self-sensing composite polymeric foam, and a transformation module that converts voltage data generated by the self-sensing composite polymeric foam in response to deformation events into ground reaction force data.

This and other aspects can include one or more of the following features, alone or in combination. For example, the transformation module may convert the voltage data to the ground reaction force data by obtaining voltage data from a plurality of locations, each location corresponding to a probe and combining the voltage data using functional data analysis and regression. As another example, the apparatus may also include a physical feedback device and an analysis module configured to compare the ground reaction force data to a profile, determine whether the ground reaction force data falls within a threshold of the profile, and provide a feedback signal when the ground reaction force data fails to fall within the threshold. The feedback signal may relate to a particular portion of a foot. In some implementations, the apparatus may also include a physical feedback device and the physical feedback device produces one of a vibration, a sound, a light pattern, and a visual display for a wearer of the shoe.

As another example, the self-sensing composite polymeric foam may conduct heat away from a foot when the foot is disposed in the shoe. As another example, the portion of the sole replaced with the self-sensing composite polymeric foam is one of an insole, a midsole, an outsole, and a sock liner. As another example, the ground reaction force data correlates to ground reaction force data obtained in a laboratory setting. As another example, the self-sensing composite polymeric foam mimics physical properties of the foam replaced.

In one general aspect, an apparatus includes a shoe having a sole, the sole having an insert that includes self-sensing composite polymeric foam, a plurality of probes disposed in the self-sensing composite polymeric foam, at least one voltage detector coupled to the plurality of probes that detects voltage data generated by the self-sensing composite polymeric foam, and a transformation module that converts voltage data generated by the self-sensing composite polymeric foam in response to deformation events into ground reaction force data. This and other aspects can include one or more of the following features, alone or in combination. For example, the self-sensing composite polymeric foam may conduct heat away from a foot when the foot is disposed in the shoe. As another example, the ground reaction force data correlates to ground reaction force data obtained in a laboratory setting. the transformation module may convert the voltage data to the ground reaction force data by obtaining voltage data from a plurality of locations, each location corresponding to a probe and combining the voltage data using functional data analysis and regression. As another example, the apparatus may also include a physical feedback device and an analysis module configured to compare the ground reaction force data to a profile, determine whether the ground reaction force data falls within a threshold of the profile, and provide a feedback signal when the ground reaction force data fails to fall within the threshold. The feedback signal may relate to a particular portion of a foot. In some implementations, the apparatus may also include a physical feedback device and the physical feedback device produces one of a vibration, a sound, a light pattern, and a visual display for a wearer of the shoe.

In one general aspect, a method includes receiving voltage data produced by a self-sensing composite polymeric foam, the self-sensing composite polymeric foam providing support and padding in the sole of a shoe, converting the voltage data to force data, comparing the force data to a profile, and transmitting, when the force data fails to fall within a threshold of the profile, a feedback signal to a physical feedback device, the feedback signal indicating a difference with the profile.

This and other aspects can include one or more of the following features, alone or in combination. For example, the feedback signal may relate to a particular portion of a foot. As another example, the feedback signal may cause the physical feedback device to play a sound. As another example, the feedback signal may cause the physical feedback device to display an image. As another example, the feedback signal causes the physical feedback device to display a light pattern. As another example, the force data may be acceleration data and converting the voltage data to acceleration data includes: the use of statistical methods such as basis expansions and regression. As another example, the force data may be pressure data and the method also includes converting the voltage to ground reaction force data, and comparing the ground reaction force data to a second profile, wherein the feedback signal further indicates a difference with the second profile. As another example, the self-sensing polymeric foam may be an insert added by the wearer of the shoe.

In one general aspect, an apparatus, comprises a shoe having foam-based padding, wherein at least a portion of foam-based padding is replaced with a self-sensing composite polymeric foam, at least one probe disposed in the self-sensing composite polymeric foam, a voltage detector coupled to the probe that detects voltage data generated by the self-sensing composite polymeric foam, and a transformation module that converts voltage data generated by the self-sensing composite polymeric foam in response to an impact event into pressure data.

This and other aspects can include one or more of the following features, alone or in combination. For example, the padding may be in a tongue of the shoe or a sidewall of the shoe. As another example, the impact event may result from kicking a ball and the apparatus further includes an analysis module configured to compare the pressure data to a kicking profile and provide feedback when the pressure data fails to fall within a threshold of the kicking profile. In some implementations, the apparatus may also include a plurality of probes, wherein each probe enables detection of voltage data at a different location in the self-sensing composite polymeric foam and wherein the analysis module us further configured to compare pressure data from each location as part of comparing the pressure data to the kicking profile.

In one general aspect, a shoe insert comprises self-sensing composite polymeric foam, a plurality of probes disposed in the composite polymeric foam, at least one voltage detector coupled to the plurality of probes, the voltage detector configured to detect voltage data generated by the self-sensing composite polymeric foam, and a microcontroller configured to store the voltage data. This and other aspects can include one or more of the following features, alone or in combination. For example, the microcontroller may include a transformation module that converts voltage data generated by the self-sensing composite polymeric foam in response to at least one of ground reaction force data, pressure data, and acceleration data. As another example, the microcontroller may include a transmitter that transmits the voltage data to another computing device having a transformation module that converts voltage data generated by the self-sensing composite polymeric foam in response to at least one of ground reaction force data, pressure data, and acceleration data. As another example, the self-sensing composite polymeric foam may be an integral portion with the plurality of probes disposed therein. As another example, the self-sensing composite polymeric foam may be a plurality of portions, each with one or more probes disposed therein.

What is claimed is:

1. A shoe comprising:
   foam-based padding, at least a portion of the foam-based padding being a self-sensing composite polymeric foam configured to exhibit a change in an electrical property when deformed and to generate an electric potential when deformed;
   at least one probe in contact with the self-sensing composite polymeric foam, the at least one probe operably coupled to a current producing device; and
   a voltage detector coupled to the at least one probe configured to detect the change in the electrical property exhibited in response to a first impact event and configured to detect the electric potential generated by the self-sensing composite polymeric foam in response to a second impact event, the first impact event occurring over a longer time period than the second impact event.

2. The shoe of claim 1, wherein the electrical property is a decrease in resistance.

3. The shoe of claim 1, the voltage detector is further configured to:
   obtain electric potential data from a plurality of locations, each location corresponding to a probe; and
   combining the electric potential data using statistical methods.

4. The shoe of claim 3, the voltage detector is further configured to:
   obtain change data for the electrical property from the plurality of locations, the electric potential data and the change data being electric data; and
   combine the electric data using statistical methods.

5. The shoe of claim 1, wherein the voltage detector detects the electric potential from a plurality of impact events and the shoe further comprises:
   at least one controller; and
   at least one memory storing instructions that, when executed by the at least one controller, cause the at least one controller to:
      compare the electric potential detected from the plurality of impact events to a profile to determine whether the electric potential detected falls within a threshold of the profile, and
      provide a feedback signal to a physical feedback device when the electric potential detected fails to fall within the threshold.

6. The shoe of claim 5, wherein the feedback signal is adapted to relate to a particular portion of a foot.

7. The shoe of claim 5, wherein the physical feedback device produces one of displayed text, a vibration, a sound, a light pattern, or a visual display.

8. The shoe of claim 5, wherein the at least one memory stores instructions to wirelessly transmit the feedback signal to the physical feedback device, the physical feedback device being remote from the shoe.

9. The shoe of claim 1, wherein the self-sensing composite polymeric foam mimics physical properties of the foam-based padding.

10. An apparatus comprising:
    padding for a sole of a shoe, the padding including at least one region of self-sensing composite polymeric foam that exhibits a change in an electrical property in response to deformation and generates an electric potential in response to deformation;
    at least one probe in contact with the self-sensing composite polymeric foam;
    a voltage detector coupled to the at least one probe;
    a controller; and
    memory storing instructions that, when executed by the controller, causes the controller to:
       collect first data representing electrical potential data for a set of repeated impact events, and
       collect second data representing a change in the electrical property for a deformation event, wherein the deformation event occurs over a longer time period than any impact event in the set of repeated impact events.

11. The apparatus of claim 10, wherein the memory further stores instructions that, when executed by the controller, cause the controller to:
   determine that the first data fails to fall within a threshold of a profile by comparison of the first data to the profile; and
   transmit a feedback signal to a physical feedback device responsive to determining that the first data fails to fall within the threshold.

12. The apparatus of claim 11, wherein the profile represents a sprinting stride, a hurdle stride, or a walking stride.

13. The apparatus of claim 12, wherein the feedback signal is adapted to relate to a particular portion of a foot.

14. The apparatus of claim 10, wherein the memory further stores instructions that, when executed by the controller, cause the controller to:
   determine that the second data fails to fall within a threshold of a profile by comparison of the second data to the profile; and
   transmit a feedback signal to a physical feedback device responsive to determining that the second data fails to fall within the threshold.

15. The apparatus of claim 10, wherein the self-sensing composite polymeric foam represents a majority of surface area in the sole of the shoe.

16. The apparatus of claim 10, wherein the self-sensing composite polymeric foam is in an insert added by a wearer of the shoe.

17. A wearable apparatus comprising:
   a self-sensing composite polymeric foam sensor configured to exhibit a change in an electrical property when deformed and to generate an electric potential when deformed;
   a plurality of probe sets in contact with the self-sensing composite polymeric foam sensor, at least one probe in each probe set being a voltage detector configured to detect the change in the electrical property and configured to detect the electric potential generated; and
   a memory configured to:
      store electrical potential data detected by the voltage detector responsive to a series of first impact events to the self-sensing composite polymeric foam sensor, and
      store change data for the electrical property detected by the voltage detector responsive to a second impact event to the self-sensing composite polymeric foam sensor,
      wherein the second impact event occurs over a longer time period than any of the first impact events.

18. The wearable apparatus of claim 17, further comprising:
   a controller configured to transmit the electrical potential data or the change data to a computing device.

19. The wearable apparatus of claim 18, wherein the computing device is a smart watch, smart phone, tablet, or personal computer.

20. The wearable apparatus of claim 17, wherein the self-sensing composite polymeric foam sensor is included in a sole insert added by a wearer of a shoe.

* * * * *